United States Patent
Li et al.

(10) Patent No.: US 11,492,609 B2
(45) Date of Patent: Nov. 8, 2022

(54) ADAPTIVE ELECTRODE ARRANGEMENT AND METHOD

(71) Applicant: AMGEN INC., Thousand Oaks, CA (US)

(72) Inventors: Chuck Z. Li, Thousand Oaks, CA (US); Brandon Zachary Sarich, Thousand Oaks, CA (US); Phillip Ng, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 326 days.

(21) Appl. No.: 16/639,016

(22) PCT Filed: Aug. 7, 2018

(86) PCT No.: PCT/US2018/045587
§ 371 (c)(1),
(2) Date: Feb. 13, 2020

(87) PCT Pub. No.: WO2019/036232
PCT Pub. Date: Feb. 21, 2019

(65) Prior Publication Data
US 2020/0224188 A1   Jul. 16, 2020

Related U.S. Application Data

(60) Provisional application No. 62/546,445, filed on Aug. 16, 2017.

(51) Int. Cl.
*C12M 3/00*   (2006.01)
*C12N 5/00*   (2006.01)
(Continued)

(52) U.S. Cl.
CPC ............... *C12N 13/00* (2013.01); *C12M 1/42* (2013.01); *C12M 23/12* (2013.01); *C12M 35/02* (2013.01);
(Continued)

(58) Field of Classification Search
CPC .... C12M 35/02; C12M 23/12; C12N 2529/00
See application file for complete search history.

(56) References Cited

U.S. PATENT DOCUMENTS 2,776,257 A   1/1957   Affleck
3,873,437 A   3/1975   Pulver
(Continued)

FOREIGN PATENT DOCUMENTS

WO   WO-9309838 A1   5/1993
WO   WO-0034434 A1   6/2000
(Continued)

OTHER PUBLICATIONS

International Search Report for International Application No. PCT/US2018/045587, dated Oct. 25, 2018.
(Continued)

*Primary Examiner* — Nathan A Bowers
(74) *Attorney, Agent, or Firm* — Marshall, Gerstein & Borun LLP

(57) ABSTRACT

A well for electrically stimulating at least one cell. The well includes a bottom portion and comprises an adaptive electrode arrangement for introducing an electric field into the well. The adaptive electrode arrangement includes a pair of electrodes disposed within the well. Each electrode of the pair of electrodes has a distal end and is independently and axially displaceable relative to the other electrode and the bottom portion of the well. The distal end of each electrode
(Continued)

of the pair of electrodes is in contact with the bottom portion of the well, ensuring a uniform and constant electric field is applied within the well.

8 Claims, 13 Drawing Sheets

(51) Int. Cl.
    *C12N 13/00*     (2006.01)
    *C12M 1/32*     (2006.01)
    *C12M 1/42*     (2006.01)
    *C12N 5/077*     (2010.01)
    *G01N 33/50*     (2006.01)

(52) U.S. Cl.
    CPC ....... *C12N 5/0657* (2013.01); *G01N 33/5008* (2013.01); *G01N 33/5061* (2013.01); *C12N 2506/45* (2013.01); *C12N 2529/00* (2013.01)

(56) References Cited

U.S. PATENT DOCUMENTS

| | | | |
|---|---|---|---|
| 4,695,547 A | 9/1987 | Hilliard et al. | |
| 4,882,281 A | 11/1989 | Hilliard et al. | |
| 5,232,856 A | 8/1993 | Firth | |
| 5,432,086 A | 7/1995 | Franzl et al. | |
| 6,461,860 B2 | 10/2002 | Mathes et al. | |
| 6,485,963 B1 | 11/2002 | Wolf et al. | |
| 6,673,597 B2 | 1/2004 | Wolf et al. | |
| 6,815,197 B2 | 11/2004 | Boven et al. | |
| 7,169,609 B2 | 1/2007 | Negulescu et al. | |
| 7,373,968 B2 | 5/2008 | Oldenburg | |
| 7,732,204 B2 | 6/2010 | Donahue | |
| 7,854,896 B2 | 12/2010 | Tyndorf et al. | |
| 8,101,401 B2 | 1/2012 | Muller-Hartmann et al. | |
| 8,455,228 B2 | 6/2013 | Jaroszeski et al. | |
| 8,940,146 B2 | 1/2015 | Trones et al. | |
| 9,149,806 B2 | 10/2015 | Collins | |
| 9,279,797 B2 | 3/2016 | Clements et al. | |
| 9,447,447 B2 | 9/2016 | Yasuda et al. | |
| 2005/0089991 A1 | 4/2005 | Walters et al. | |
| 2006/0115888 A1 | 6/2006 | Gamelin et al. | |
| 2014/0277231 A1 | 9/2014 | Berneman | |
| 2015/0313704 A1 | 11/2015 | Thavandiran et al. | |
| 2015/0315539 A1 | 11/2015 | Villanueva et al. | |
| 2015/0368604 A1* | 12/2015 | Mizuno | C12N 13/00 435/461 |
| 2016/0282338 A1 | 9/2016 | Miklas et al. | |

FOREIGN PATENT DOCUMENTS

| | | |
|---|---|---|
| WO | WO-2010129725 A1 | 11/2010 |
| WO | WO-2011050009 A1 | 4/2011 |

OTHER PUBLICATIONS

Written Opinion for International Application No. PCT/US2018/045587, dated Oct. 25, 2018.

Jason W. Miklas et al., "Engineering Cardiac Tissues from Pluripotent Stem Cells for Drug Screening and Studies of Cell Maturation", Israel Journal of Chemistry, XP055515033, Sep. 18, 2013.

\* cited by examiner

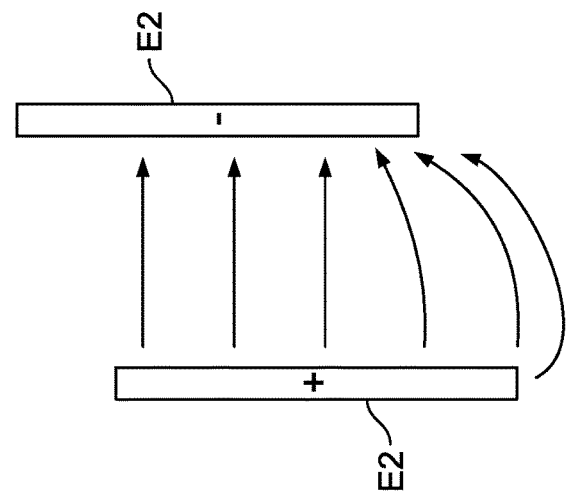
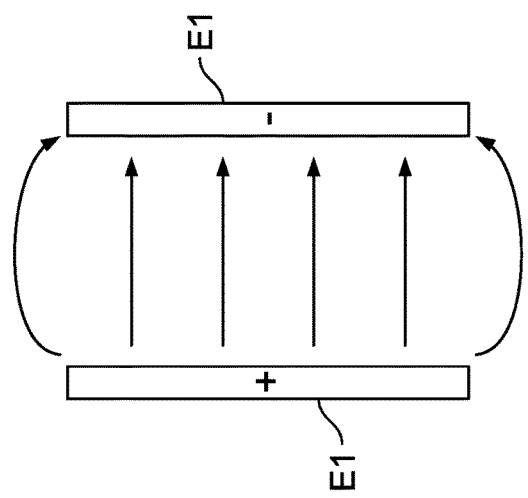
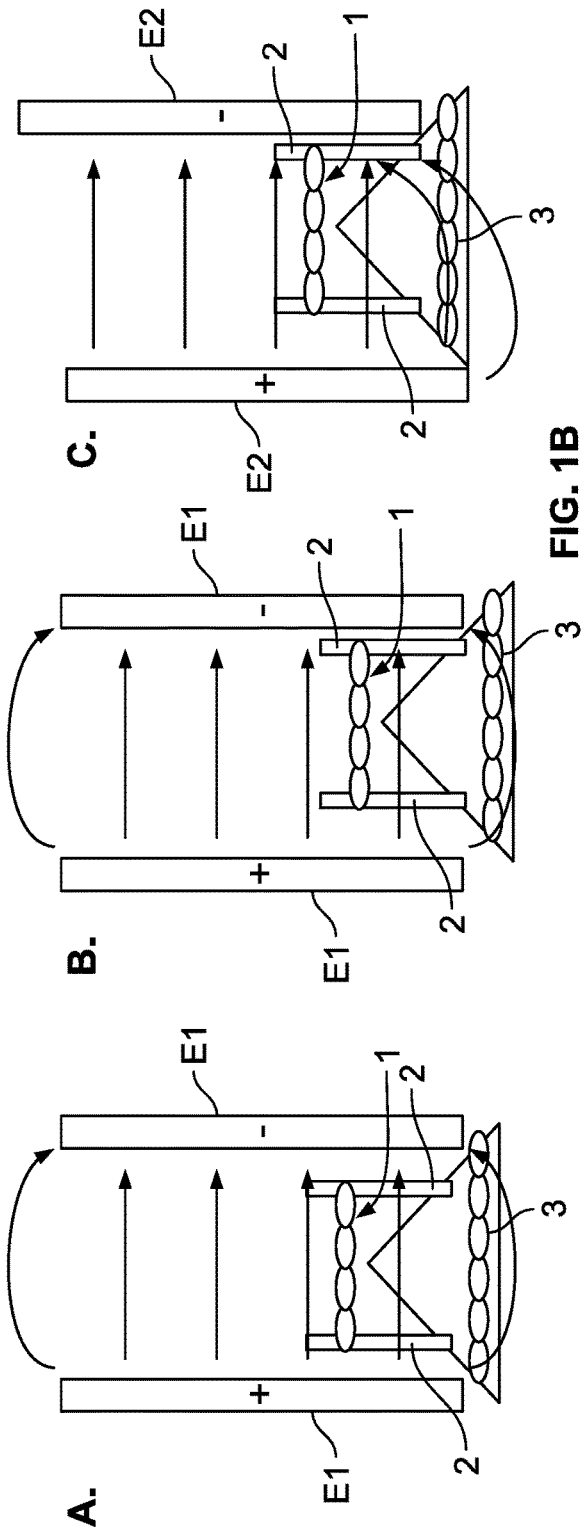
FIG. 1A
FIG. 1B

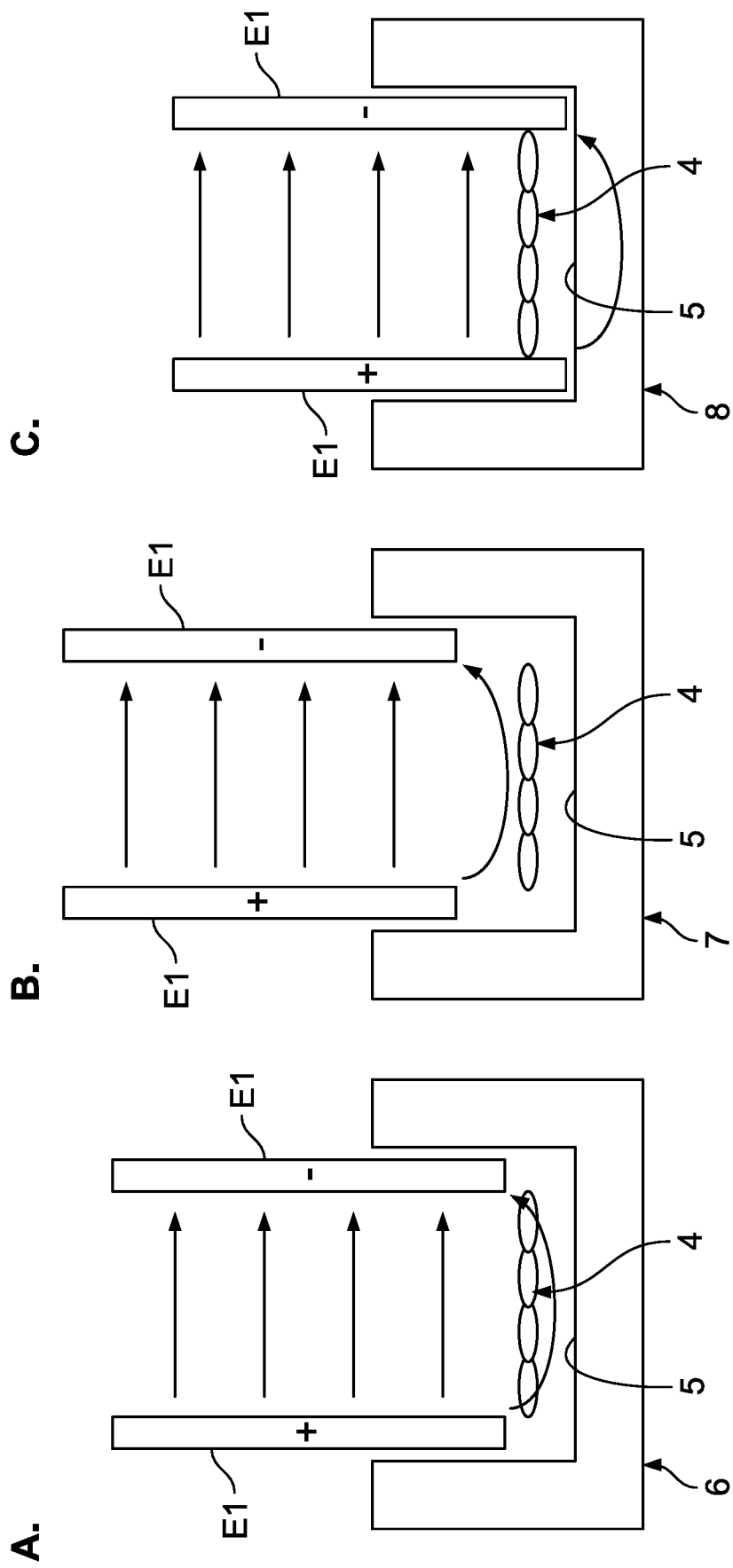

ADAPTIVE ELECTRODE ARRANGEMENT AND METHOD

CROSS-REFERENCE TO RELATED APPLICATION

This is the United States National Phase of PCT/US2018/045587, filed Aug. 7, 2018, which claims the priority benefit of U.S. Provisional Patent Application No. 62/546,445, filed Aug. 16, 2017, the entire contents of each of which are hereby incorporated herein by reference.

FIELD OF THE DISCLOSURE

The present disclosure generally relates to electrode arrangements for wells and well-plates and, more particularly, an adaptive electrode arrangement and method for introducing an electric field to a sample well or a plurality of wells of a microwell plate.

BACKGROUND

Various cells, such as cardiomyocytes, are often used in an in vitro setting in the study of cardiac disease models. The sources of these cells can originate from primary isolated heart muscles or differentiated from induced pluripotent stem cells (iPSCs). The isolated primary cells, depending on maturation stage (i.e., embryonic versus adult), may not be able to contract autonomously as in the whole heart due to the absence of pacer cell signaling or the functions of certain ion channels. Thus, external electrical pacing is required to properly elicit the contractile properties of these cells to resemble their physiological behavior in vivo. The contractile function of the cells, which is a key metric in assessing new therapies, can be measured using various assay methods such as calcium flux or direct force measurement.

External electrical pacing has also been cited to affect the maturation of iPSC derived cardiomyocytes in culture. Namely, early onset of stimulation can modify beating rhythm and contraction propagation profiles of the cardiomyocytes. In addition, external pacing of the cells helps the synchronization in measurement, which results in better signal window and data interpretation.

Implementation of electrical pacing for cell maturation typically requires the colocation of stimulating electrodes and cell culture vessel in an incubator. Unfortunately conventional electrode array designs require a stimulation head and possibly integrated electronics, they are often impractical for routine, everyday use in such settings due to their size and the humidified environment of the incubator.

The application of electric field stimulation or pacing of cells is not only limited to cardiomyocytes, but is also in the study of voltage-gated ion channels or membrane potential. In the field of drug discovery, rigid, multi-array field stimulation electrode designs have been produced before for this purpose. However, such conventional electrode designs typically require precisely measuring the depth of a well to understand how deep the electrodes must be lowered into the well to affect a uniform electric field across the cells in the well, for example. In one example, the uniform electric field is the field between overlapping parallel electrodes. The problem becomes even more obvious if the subjected cells are at or near the bottom of the well in which case it requires lowering the electrodes to reach the bottom of the well to affect the uniform electric field. Else, these cells between the electrodes are only being stimulated by the electric field fringes and result in non-uniform in vivo physiological behavior, thus limiting the quality of assay. Further, a major shortcoming of many conventional electrode designs is the inability to incorporate reagent dispensing while simultaneously conducting the electrical stimulation of the cells. Such inability has limited the types of assays to interrogate cellular mechanism, experiment throughput and the study of early compound kinetics, for example.

SUMMARY

Disclosed herein are devices and methods that provide for providing an electrical stimulus across a population of cells in a well, regardless of the substrate geometry of the well.

In accordance with a first aspect, a well for electrically stimulating at least one cell has a bottom portion. The well comprises an adaptive electrode arrangement for introducing an electric field into the well, and the adaptive electrode arrangement includes a pair of electrodes disposed within the well, the pair of electrodes having a distal end and independently and axially displaceable relative to each other and the bottom portion of the well. The distal end of each electrode of the pair of electrodes is in contact with the bottom portion of the well, ensuring a uniform and constant electric field is applied within the well.

In accordance with a second aspect, a microwell plate assembly comprises a microwell plate having a plurality of wells, and each well of the plurality of wells has a bottom portion. The microwell plate assembly also includes an array of adaptive electrode arrangements for introducing an electric field into each well of the plurality of wells. Each adaptive electrode arrangement includes a pair of electrodes disposed within the well of the plurality of wells, and each electrode of the pair of electrodes has a distal end and is independently and axially displaceable relative to each other and the bottom portion of the well; The distal end of each electrode of the pair of electrodes is in contact with the bottom portion of the well, ensuring a uniform and constant electric field is applied within the well.

In accordance with a third aspect, an adaptive electrode arrangement for a microwell plate comprises one of a circuit board or a cover plate and a pair of electrodes coupled to one of the circuit board or the cover plate and adapted to be disposed within a well of a plurality of wells. The pair of electrodes is independently and axially displaceable relative to a bottom portion of the well and each other, and each electrode of the pair of electrodes has a distal end. The distal end of each electrode of the pair of electrodes is adapted to be in constant contact with the bottom portion of the well when disposed within the well, ensuring a uniform and constant electric field is applied within the well.

In accordance with yet another aspect, a method of introducing an electric field into a well comprises disposing a pair of electrodes within the well and independently and axially displacing each electrode of the pair of electrodes relative to each other to enable a distal end of each electrode of the pair of electrodes to contact a bottom portion of the well. The method further comprises maintaining constant contact of the distal end of each electrode of the pair of electrodes with the bottom portion of the well and applying a uniform electric field within the well.

In accordance with yet another aspect, a method of synchronizing a behavior of a population of cells by introducing an electric field into a well of a plurality of wells of a microwell plate comprises adding the population of cells in a well of the plurality of wells. The method also includes disposing a pair of electrodes within the well of the plurality of wells, and independently and axially displacing each electrode of the pair of electrodes relative to each other to enable a distal end of each electrode of the pair of electrodes to contact a bottom portion of the well. The method further includes maintaining constant contact of the distal end of each electrode of the pair of electrodes with the bottom portion of the well, and applying a uniform electric field within the well, such that the behavior of each cell of the population of cells is approximately synchronized.

In accordance with still yet another aspect, a method of altering a membrane potential of a cell by introducing an electric field into a well of a microwell plate assembly comprises adding a cell in a well of the microwell plate assembly and disposing a pair of electrodes within the well. The method also includes independently and axially displacing each electrode of the pair of electrodes relative to each other to enable a distal end of each electrode of the pair of electrodes to contact a bottom portion of the well. The method further includes maintaining constant contact of the distal end of each electrode of the pair of electrodes with the bottom portion of the well, and applying a uniform electric field within the well, such that the membrane potential of the cell is excited.

In accordance with yet another aspect, a cell incubator system comprises a container and a microwell plate assembly disposed within the container. The microwell plate assembly may include a microwell plate having a plurality of wells and an array of electrode arrangements for introducing an electric field into each well of the plurality of wells. Each electrode arrangement may have a pair of electrodes and one of a cover plate or a circuit board to which the pair of electrodes is coupled. Each of the cover plate and the circuit board may have an opening for enabling solution to be dispensed into the well while the electric field is being applied within the well.

In accordance with still yet another aspect, a microwell plate assembly adapted to be one or more of disposed in a container of a cell incubator system or coupled to cell culture support utilities may comprise a microwell plate having a plurality of wells and an array of electrode arrangements for introducing an electric field into each well of the plurality of wells. Each electrode arrangement may have a pair of electrodes and one of a cover plate or a circuit board to which the pair of electrodes is coupled. Each of the cover plate and the circuit board may have an opening for enabling solution to be dispensed into the well while the electric field is being applied within the well.

In further accordance with any one or more of the foregoing aspects and methods, one or more of the well, the microwell plate assembly, the adaptive electrode arrangement, and related methods may include any one or more of the following forms or method steps.

In one form, the well may further comprise one or more of at least one micropost, a microwire formed around the at least one micropost, a bottom surface, a base disposed on the bottom surface, and a ramp, one of extending or separate from the base, to which the at least one micropost is attached. In addition, the bottom portion may include one or more of the bottom surface, the base, and the ramp, such that the distal end of each electrode of the pair of electrodes is in contact with one of the bottom surface, the base, or the ramp of the well. In addition, the well may further comprise at least one micropost having a length, and each electrode of the pair of electrodes may include a length that is at least about the same or greater than the length of at least one micropost. Further, a circuit board to which the adaptive electrode arrangement is integrated may be coupled to the well. The circuit board may include a plurality of openings and a through-hole disposed on either side of each opening, the through-hole for receiving a proximal end of each electrode of the pair of electrodes. A spring for securing each proximal end of each electrode of the pair of electrodes to the circuit board and enabling each electrode to be independently and axially displaceable may also be included. In addition, each electrode of the pair of electrodes may be disposed on either side of an opening of the plurality of openings of the circuit board.

In other forms, the adaptive electrode arrangement may further include a cover plate having a pair of through-holes, each through-hole for receiving a proximal end of each electrode of the pair of electrodes. Each electrode may be axially displaceable along an axis of the cover plate, which allows each electrode to move relative to one or more of the bottom portion of the well and the cover plate. In addition, the adaptive electrode arrangement may further include a cover plate having a distal portion, and each electrode of the pair of electrodes having a proximal end. A spring with a first end attached to the distal portion of the cover plate and a second end coupled to the proximal end of each electrode of the pair of electrodes may also be included to couple each electrode to the cover plate, allowing each electrode to be axially displaceable along an axis of the cover plate. Still further, the distal end of each electrode of the pair of electrodes may be in constant contact with the bottom portion of the well, and the bottom portion of the well may include one or more of a bottom surface, a base, or a ramp of the well. In addition, each cover plate above the well may include an opening disposed between the pair of electrodes to allow for dispensing of solution within the well while the electric field is being applied within the well.

In still other forms, a first spring having a first portion and a second portion is included. The first portion may be coupled to a proximal end of a first electrode disposed on a first side of the circuit board, and the second portion may be coupled to a proximal end of a second electrode disposed on the first side of the circuit board. The spring may be for securing the first and second electrodes to the circuit board and enabling axial displacement of the first and second electrodes. In addition, a second spring having a first portion and a second portion may also be included. The first portion may be coupled to a proximal end of a third electrode disposed on a second side of the circuit board opposite the first electrode, and the second portion may be coupled to a proximal end of a fourth electrode disposed on the second side of the circuit board opposite the second electrode. The spring may be for securing the third and fourth electrodes to the circuit board and enabling axial displacement of the third and fourth electrodes. So configured, the first and third electrodes may be disposed on either side of a first opening of the plurality of openings of the circuit board, and the second and fourth electrodes may be disposed on either side of a second opening of the plurality of openings of the circuit board. The first and third electrodes may form a pair of electrodes of a first adaptive electrode arrangement of the array of adaptive electrode arrangements, and the second and fourth electrodes may form a pair of electrodes of a second adaptive electrode arrangement of the array of adaptive electrode arrangements.

In one form of a method, the method may comprise providing a length of each electrode of the pair of electrodes that is at least about equal to or greater than a length of a micropost disposed in the well. In addition, independently and axially displacing each electrode of the pair of electrodes relative to each other may comprise providing one of at least one through-hole disposed within one of a lid or a cover plate for receiving a proximal end of each electrode of the pair of electrodes, or at least one spring for coupling the proximal end of each electrode to one of a lid or a cover plate. Further, maintaining constant contact of a distal end of each electrode of the pair of electrodes with the bottom portion of the well may comprise providing at least one through-hole within a cover plate for receiving a proximal end of each electrode or at least one spring having a first end attached to the cover plate and a second end attached to the proximal end of each electrode of the pair of electrodes, allowing the distal end of each electrode to move relative to the cover plate and each other to accommodate different heights and/or geometric configurations of the bottom portion of the well.

In another form of the method, the method may further comprise integrating a pair of electrodes into a circuit board of a microwell plate assembly by one or more of at least one spring or at least one through-hole disposed within the circuit board before disposing the pair of electrodes within the well. The method may also include providing an array of adaptive electrode arrangements, each adaptive electrode arrangement having a pair of electrodes and the well is one well of a plurality of wells of a microwell plate assembly, and controlling stimulation inputs by wiring the pairs of electrodes in parallel or in series to one or multiple pulse generators and amplifiers through the circuit board. Still further, the method may also comprise dispensing solution through at least one opening disposed in one or more of a circuit board of a microwell plate assembly or a cover plate coupled to the pair of electrodes while simultaneously applying the electric field within the well of the plurality of wells. Further, maintaining constant contact of the distal end of each electrode of the pair of electrodes within the bottom portion of the well may include preventing cells adapted to be disposed within the well from being stimulated by a fringe of an electric field. In another example, maintaining constant contact of the distal end of each electrode of the pair of electrodes within the bottom portion of the well may comprise maintaining constant contact of the distal end of each electrode with the bottom portion regardless of a depth of different areas of the bottom portion of the well.

In another form, independently and axially displacing each electrode of the pair of electrodes relative to each other to enable a distal end of each electrode of the pair of electrodes to contact a bottom portion of the well may comprise displacing a distal end of a first electrode of the pair of electrodes to be in contact with the bottom portion of the well at one of a lower depth than, a same depth as, or a higher depth than a distal end of the second electrode of the pair of electrodes in contact with the bottom portion of the well.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

FIG. 1A depicts exemplary electrical fields that may be generated between electrodes;

FIG. 1B depicts exemplary electric stimulation to cells on cardiac microwires formed between electrodes based on the electrode positions;

FIG. 1C depicts exemplary electric stimulation to cells in various wells having fixed height electrodes;

DETAILED DESCRIPTION

Provided herein are devices that enable the application of an electric field to, for example, a population of cells, in a well, wherein the electric field is uniform and/or extended despite the geometry of the substrate of the well. The disclosed devices and associated methods dispense of the necessity of measuring the well depth to precisely position the electrodes that provide the electric field. Furthermore, the disclosed apparatuses and methods virtually eliminate the possibility of cells not receiving the electric signal because the applied electric field reaches cells that have, for example, fallen into a bottom area or fringes of the wells. Furthermore, disclosed embodiments permit not only the ability to culture easily cells that have been electrically stimulated, but for permit reagent dispensing, even while simultaneously conducting the electrical stimulation of the cells. As such, electrical stimulation that can induce certain cell types to differentiate and mature can be applied to cells, and the cells cultured in conventional cell incubators.

Figure 1D:
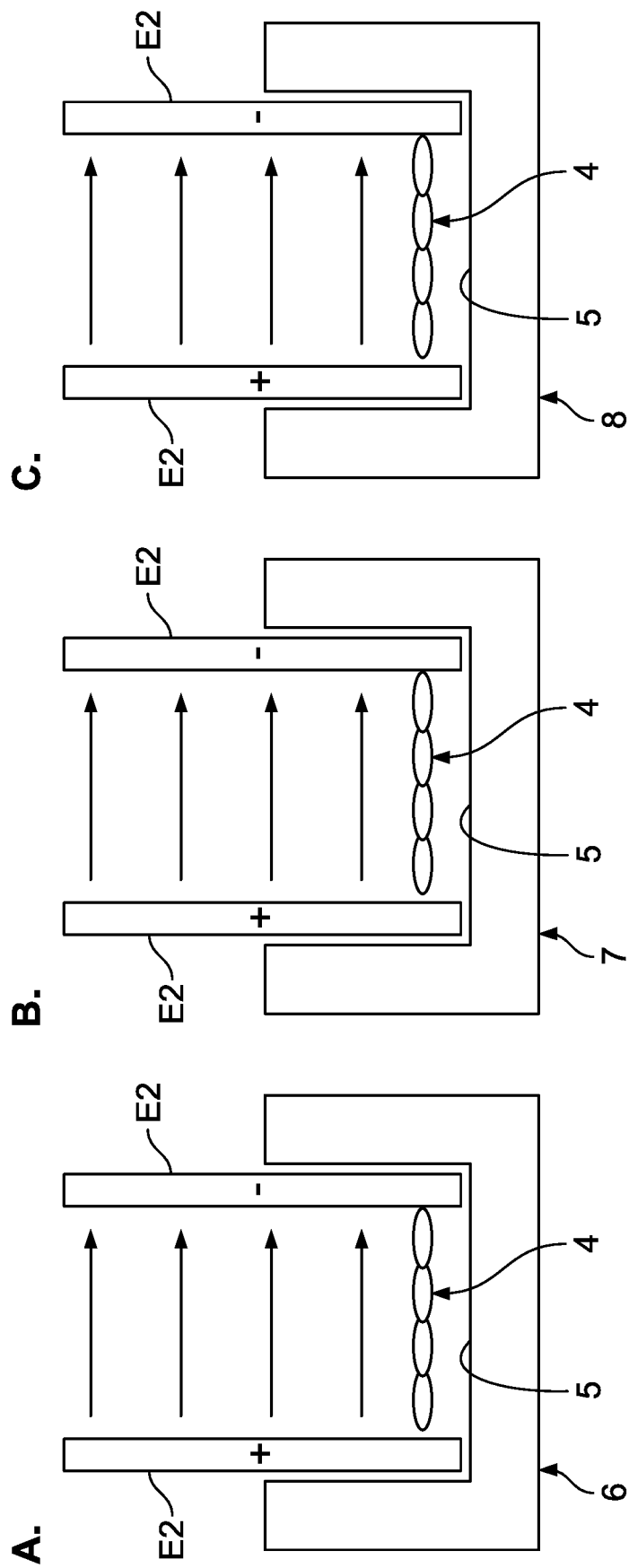
FIG. 1D depicts exemplary electric fields delivered to cells in various wells having adaptive electrodes.

FIGS. 1A-1D show some of the challenges of delivering an electric field using electrodes in a vessel, such as a well of a microwell plate. FIG. 1A shows the electrical field that is generated between electrodes. In FIG. 1A (A), the electrodes E1 are fixed into position. When an electric field is generated between them, the field is substantially uniform between the bodies of the electrodes E1 (as represented by parallel arrows). However, at the proximal and distal ends of the electrodes E1, an electric field is still present, but is not substantially uniform (represented by the curved arrows). In FIG. 1A (B), a pair of adaptive (offsetting) electrodes E2 is shown. When the electrodes E2 are in this position, the generated electric field remains substantially uniform (parallel arrows) where the two electrodes E2 are parallel o, or overlap, each other; however, where they are off-set, such as at the bottom of the electrodes, a field still passes between the electrodes E2, but is not substantially uniform.

FIG. 1B shows how these electrode positions deliver electric stimulation to cells on cardiac microwires. Cardiac microwires are cultured cardiomyocytes that make a bridge of cells ("wire") 1 between two posts 2 that are placed in the well. The cells form these wires by migrating from the floor of the well, up the posts 2, and then form the wire 1. Such configurations are valuable in ascertaining cardiomyocyte activity because they reproducibly mimic morphologic and functional properties of adult tissue. The cardiac microwire device is shown in FIG. 1B as two vertical horizontal posts 2 between the electrodes E1 (labeled "+" and "−"). The oval shapes represent cardiac myocytes. When fixed electrodes E1 are perfectly centered in a well containing the microwire apparatus and an electric field is passed between them (FIG. 1B(A)), the cells forming the wire (near the top of the microwire device), receive a substantially uniform electric field (parallel arrows). Cells at the bottom of the well 3 are also electrically stimulated, but receive a non-uniform electric field (curved arrow). However, if the fixed electrodes E1 are off-center (FIG. 1B(B)), the electrodes E1 are physically obstructed from properly immersing into the well, and the cells at the bottom of the well 3 receive an even weaker signal because they are farther away from the electrodes E1; furthermore, the electric field is also non-uniform (curved arrow). To compensate for possible misalignment, adaptive electrodes E2 can be used (FIG. 1B(C)). Electrodes E2 from this electrode configuration accommodate the physical obstruction and reach as far to the bottom as possible, independently, thus extending the electric field and keeping a majority of the cells in the uniform portion of the electric field (parallel arrows) and yet still able to cover the bottom-most cells 3 on its fringe, albeit the delivered electric field is not uniform (curved arrows).

The problem is more straight-forward when cells to be electrically stimulated form cell layers 4 on the floor 5 of the wells 6, 7, 8, as shown in FIG. 1C, showing the situation encountered with fixed height electrodes E1. Due to manufacturing imperfections, a multiwell plate has uneven well bottom 5 heights of various wells 6, 7, 8. Electrical stimulation of the cells is not reproducible well-to-well because the fixed height electrodes E1 are not in contact with every well bottom 5. Thus, in some wells, such as well 6 of FIG. 1C(A), a non-uniform electric field is delivered to the cells on the well bottom 5 (curved arrow); an even weaker non-uniform signal is delivered when the electrodes E1 are farther away from the bottom 5 of the well 7, as depicted in FIG. 1C(B) (curved arrow); and a desired uniform electric field is delivered when the fixed height electrodes E1 perfectly reach the bottom 5 of the well, such as the well 8, as depicted in FIG. 1C(C) (parallel arrow).

FIG. 1D demonstrates the advantages of adaptive electrodes E2 as more specifically disclosed herein. Regardless of the well bottom 5 height of the various wells 6, 7, 8, adaptive electrodes E2 always touch the bottom 5 of each of the wells 6, 7, 8, delivering a uniform electric field (parallel arrows) to the cells 4 in the wells 6, 7, 8, as depicted in FIG. 1D(A-C). In such a configuration, the cells 4 are no longer stimulated by the field fringes of conventional fixed-height electrodes E1.

Thus, more specifically, an adaptive electrode arrangement for a well, such as a well of a microwell plate assembly, is disclosed. The adaptive electrode arrangement includes one of a circuit board or a cover plate and a pair of electrodes coupled to one of the circuit board or the cover plate. The pair of electrodes is adapted to be disposed within the well of the microwell plate assembly and is independently and axially displaceable relative to a bottom portion of the well and each other. Each electrode of the pair of electrodes has a distal end that is in constant contact with the bottom portion of the well when disposed within the well. In this way, a uniform and extended electric field is applied within the well regardless of the various geometries of the well, such as a bottom portion of the well. Said another way, the distal end of each electrode of the pair of electrodes may move relative to one of the circuit board or the cover plate to accommodate different heights and/or geometric configurations of the bottom portion of the well, ensuring the distal end of each electrode maintains constant contact with the bottom portion of the well.

Figure 2A:
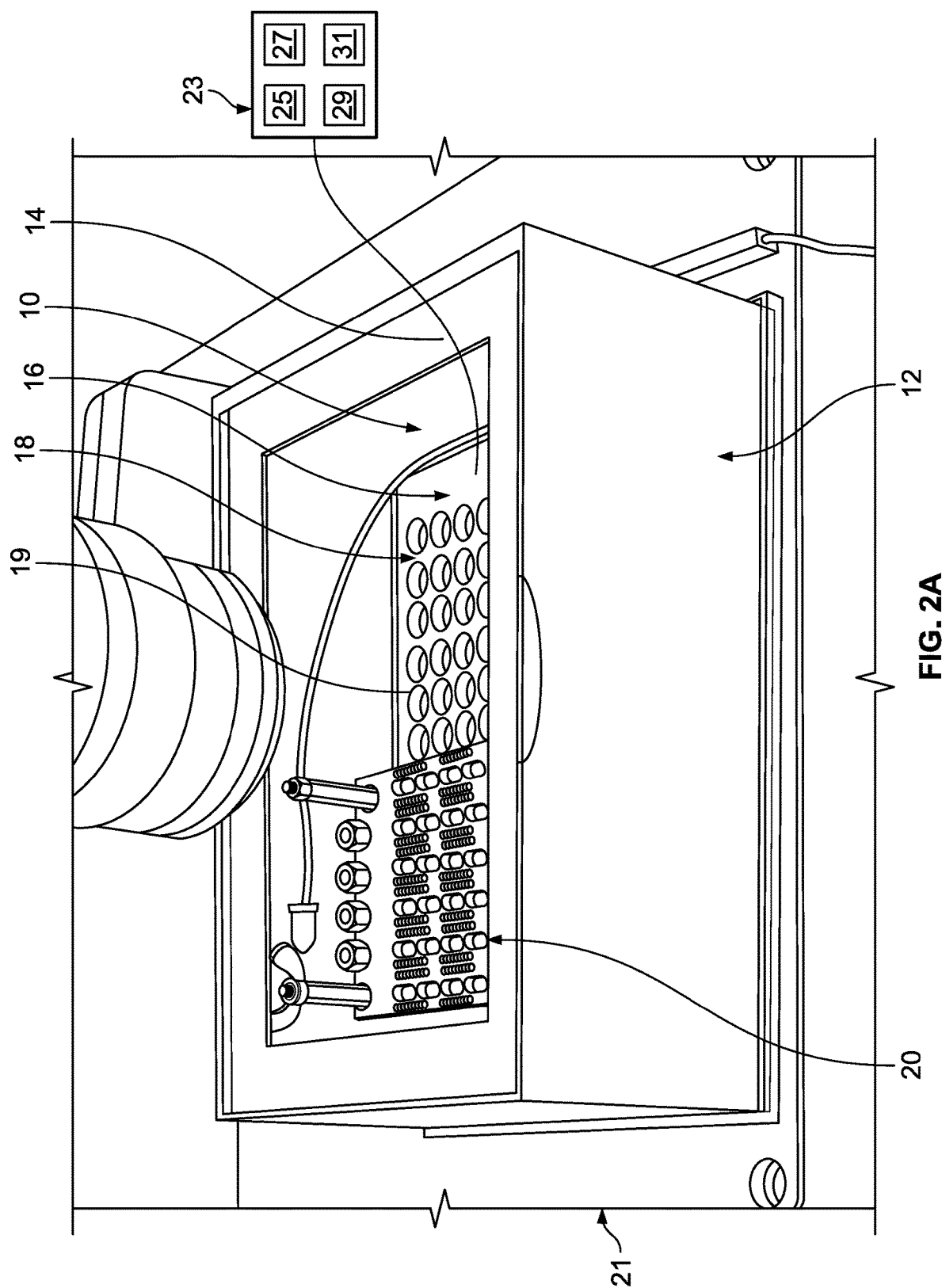
FIG. 2A is a perspective view of a microwell plate assembly according to an aspect of the present disclosure.
Figure 2B:
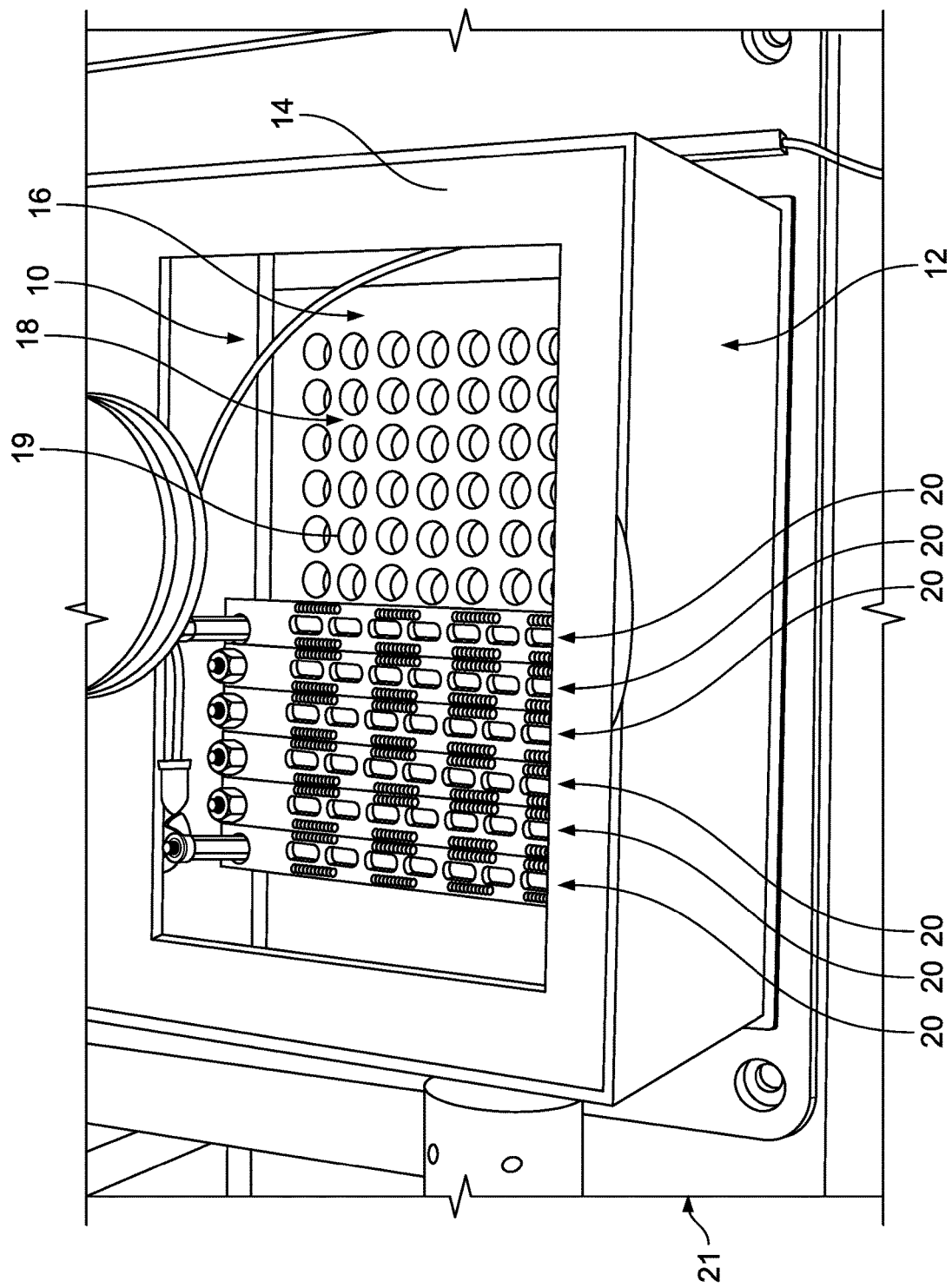
FIG. 2B is another perspective view of the microwell plate assembly of FIG. 1.

Referring now to FIGS. 2A and 2B, a microwell plate assembly 10 according to one aspect of the present disclosure is depicted. The microwell plate assembly 10 includes a body 12, such as a container, or may be disposed within the container, and a lid 14 that fits over the body 12. The microwell plate assembly 10 further includes a microwell plate 16 disposed within the body 12 and having a plurality of wells 18. An array of adaptive electrode arrangements 20 for introducing an electric field into each well 19 of the plurality of wells 18 is also included, as explained more below. As one of ordinary skill in the art understands, the well 19 is for electrically stimulating at least one cell, as also explained more below. In some examples, the container may be disposed within a cell incubator system 21, as depicted in FIG. 2A and understood by one of ordinary skill in the art. Alternatively, the microwell plate assembly 10, on itself, may be equipped with, such as coupled to, additional internal or external cell culture support utilities 23, which may include one or more of a carbon dioxide ($CO_2$) element 25, an oxygen ($O_2$) element 27, a humidified gas element 29, and one or more temperature control elements 31. In addition, the microwell plate assembly 10 may be disconnected from electrical equipment when needed, for example.

Figure 3:
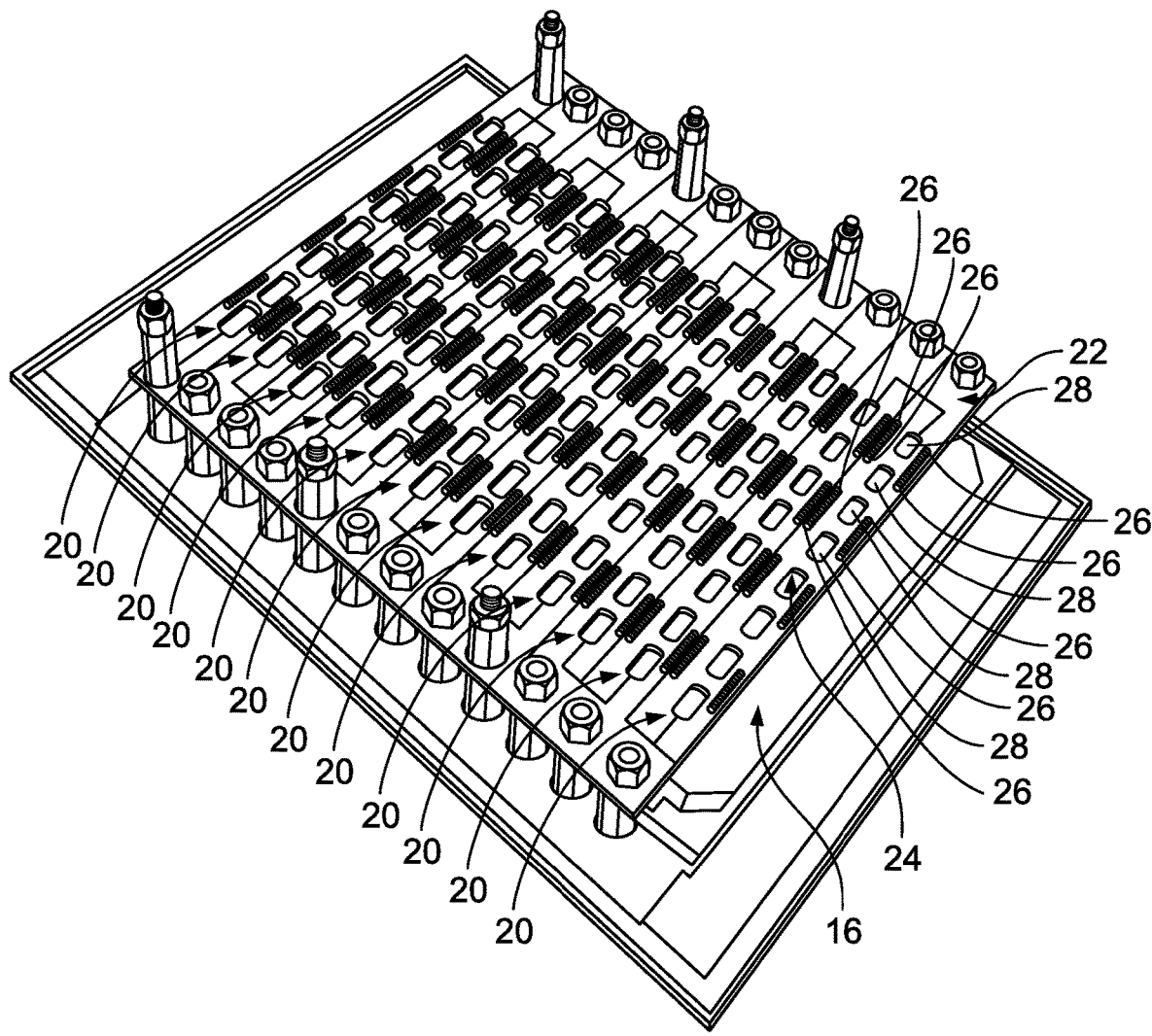
FIG. 3 is a top perspective view of a portion of the microwell plate assembly having an adaptive electrode arrangement according to another aspect of the present disclosure.

Referring now to FIG. 3, the microwell plate 16 having the plurality of wells with multiple arrays 20 of adaptive electrode arrangements coupled thereto is depicted outside of the body 12 illustrated in FIGS. 1 and 2. As depicted in FIG. 3, and in one example, there may be twelve arrays 20 of adaptive electrode arrangements coupled to the microwell plate 16. In contrast, FIGS. 2A and 2B depict six arrays 20 of adaptive electrode arrangements coupled to the microwell plate 16. Thus, as one of ordinary skill in the art will appreciate, any number of arrays of adaptive electrode arrangements may alternatively be disposed on and/or within the microwell plate 16 to introduce the electric field within each corresponding well 19 and still fall within the scope of the present disclosure. For example, 1, 2, 3, 4, 5, 6, 7, 8, 9, 10, 11, and 12 or more arrays of adaptive electrode arrangements may be coupled to the microwell plate.

In one example, the microwell plate assembly 10 may include a circuit board 22 that is coupled to the microwell plate 16 and to which the array 20 of adaptive electrode arrangements is integrated. The circuit board 22 may include a plurality of openings 24 and a through-hole 26 disposed on either side of each opening 28 of the plurality of openings 24, as partially depicted in FIG. 3.

Figure 4:
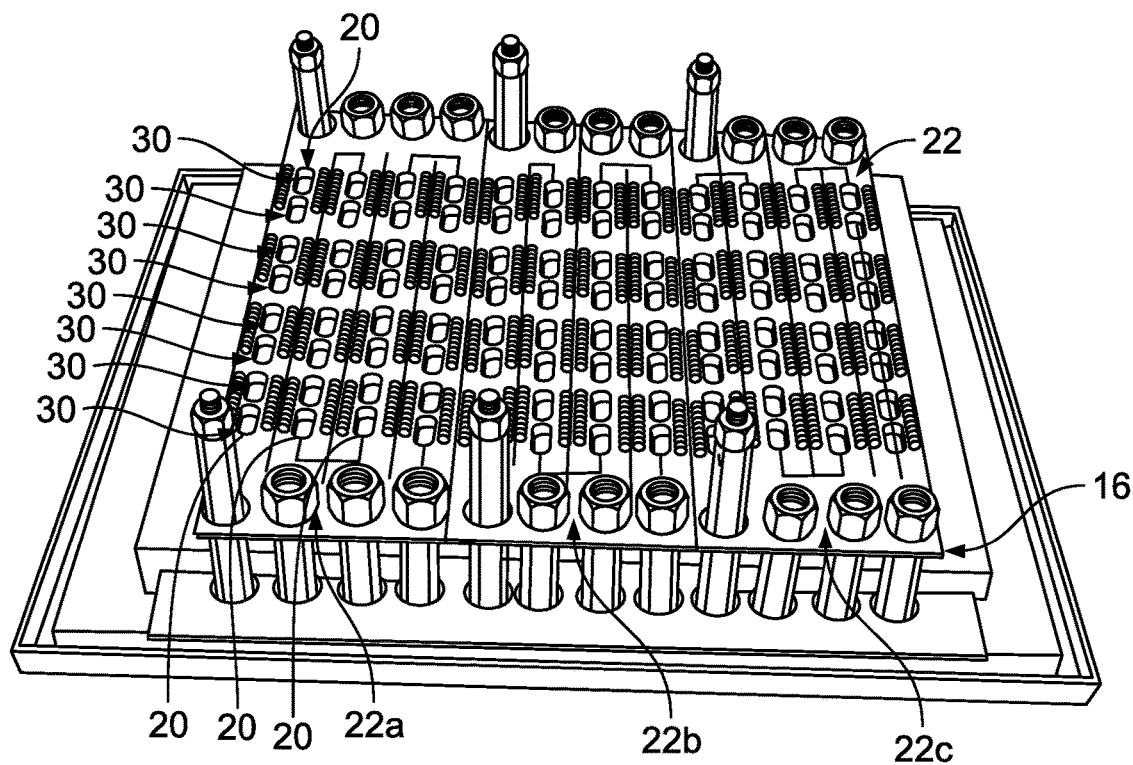
FIG. 4 is a side perspective view of the portion of the microwell plate assembly of FIG. 3.

Referring now to FIG. 4, in one example, the circuit board 22 may include multiple sections, wherein each section includes multiple arrays of adaptive electrode arrangements, and each array of adaptive electrode arrangements includes multiple adaptive electrode arrangements. More specifically, and in one example, the circuit board 22 may include three sections 22a, 22b and 22c, as depicted in FIG. 4. In this example, each of the three sections 22a, 22b and 22c of the circuit board 22 may include four arrays 20 of adaptive electrode arrangements 30, as illustrated relative to section 22a in FIG. 4. Each array 20 of adaptive electrode arrangements may include eight adaptive electrode arrangements. As one of ordinary skill in the art will appreciate, each section may alternatively include more or fewer arrays 20 of adaptive electrode arrangements and each array may alternatively include more or fewer than eight adaptive electrode arrangements and still fall within the scope of the present disclosure. For example, the circuit board 22 of FIGS. 2A and 2B includes three sections, each of which includes two arrays 20 of adaptive electrode arrangements. In addition, instead of having multiple sections, the circuit board 22 may alternatively include a single unibody (not shown) having multiple arrays of adaptive electrode arrangements, each array having more than one adaptive electrode arrangement, for example, and still fall within the scope of the present disclosure.

Figure 5:
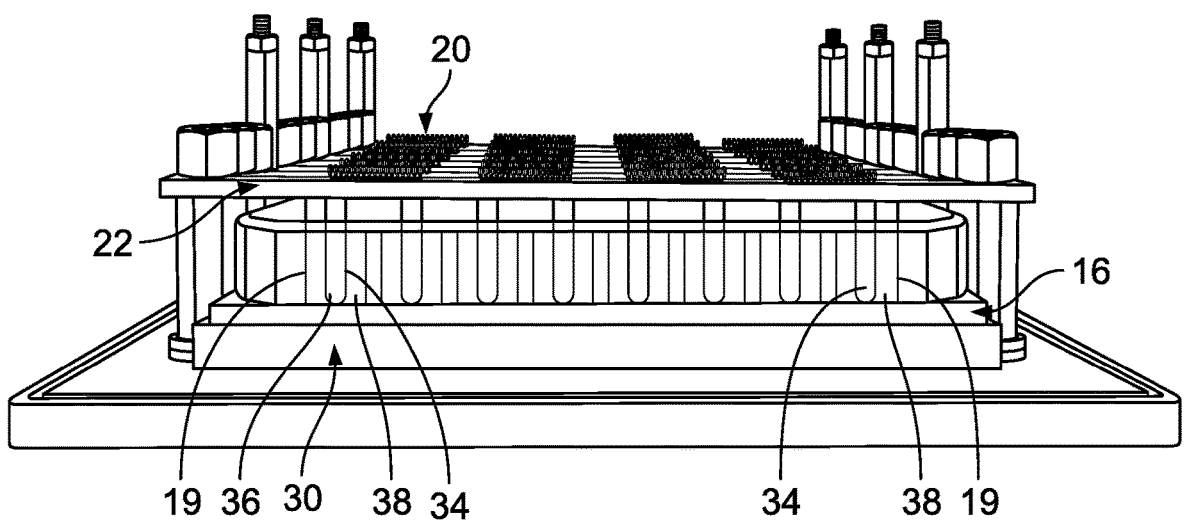
FIG. 5 is a front view of the portion of the microwell plate assembly of FIG. 4.
Figure 6:
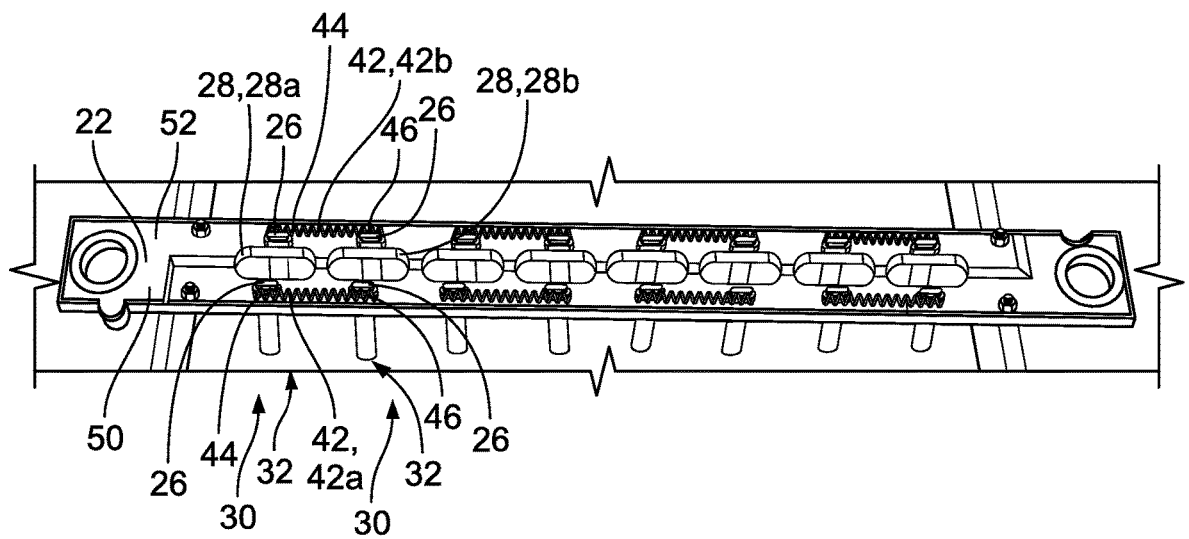
FIG. 6 is top perspective view of another portion of the microwell plate assembly of FIG. 1.
Figure 7:
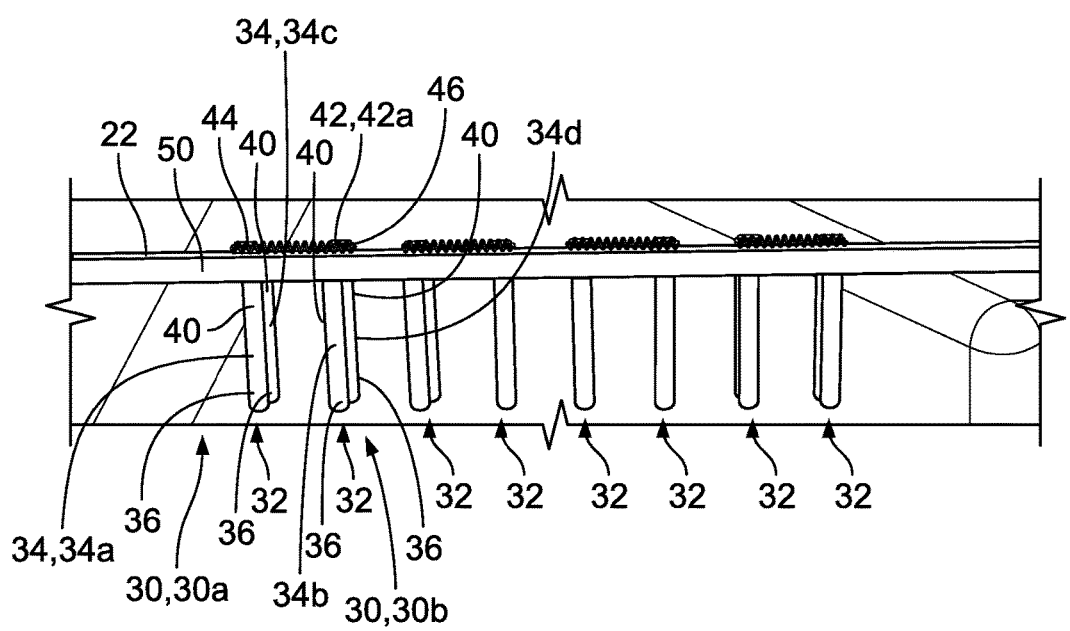
FIG. 7 is a side view of the portion of the microwell plate assembly of FIG. 6.

Referring now to FIGS. 5-7, an adaptive electrode arrangement 30 (FIG. 5) of the array 20 of adaptive electrode arrangements is depicted. Each adaptive electrode arrangement 30 introduces an electric field into the well 19 and includes a pair of electrodes 32 (FIG. 7) disposed within the well 19 of the plurality of wells 18. Each electrode 34 of the pair of electrodes 32 has a distal end 36 and is independently and axially displaceable relative to each other and a bottom portion 38 of the well 19. As a result, the distal end 36 of each electrode 34 is in constant contact with the bottom portion 38 of the well 19, ensuring a uniform and constant electric field is applied within the well 19.

As depicted in FIG. 7, each electrode 34 of the pair of electrodes 32 also includes a proximal end 40. The through-hole 26 (FIG. 6) disposed on either side of the opening 28 of the circuit board 22 receives the proximal end 40 of each electrode 34 to couple the pair of electrodes 32 to the circuit board 22.

As depicted in FIGS. 6 and 7, the microwell plate assembly 10 may further include at least one spring 42 having a first portion 44 and a second portion 46. The first portion 44 is coupled to the proximal end 40 of the electrode 34, such as a first electrode 34a (FIG. 7), disposed on a first side 50 of the circuit board 22. The second portion 46 is coupled to the proximal end 40 of another electrode, such as a second electrode 34b (FIG. 7), also disposed on the first side 50 of the circuit board 22. At least one spring 42, which may be a first spring 42a, secures the first and second electrodes 34a, 34b to the circuit board 22 and enables axial displacement of the first and second electrodes 34a, 34b relative to the bottom portion 38 (FIG. 5) of the well 19, for example.

As further depicted in FIG. 6, the microwell plate assembly 10 may further include a second spring 42b having a first portion 44 and a second portion 46. In a manner similar to the first spring 42a, the first portion 44 of the second spring 42b is coupled to the proximal end 40 of a third electrode 34c (FIG. 7) disposed on a second side 52 (FIG. 6) of the circuit board 22 opposite the first electrode 34a. The second portion 46 of the second spring 42b is coupled to a proximal end 40 of a fourth electrode 34d (FIG. 7) disposed on the second side 52 of the circuit board 22 opposite the second electrode 34b. The second spring 42b secures the third and fourth electrodes 34c, 34d to the circuit board 22 and enables axial displacement of the third and fourth electrodes 34c, 34d. So configured, the first and third electrodes 34a, 34c, respectively, are disposed on either side of a first opening 28a (FIG. 6) of the plurality of openings and the second and fourth electrodes 34b, 34d, respectively, are disposed on either side of a second opening 28b (FIG. 6). In this way, the first and third electrodes 34a, 34c, respectively, form a pair of electrodes of a first adaptive electrode arrangement 30a. Likewise, the second and fourth electrodes 34b, 34d, respectively, form a pair of electrodes of a second adaptive electrode arrangement 30b.

Figure 8A:
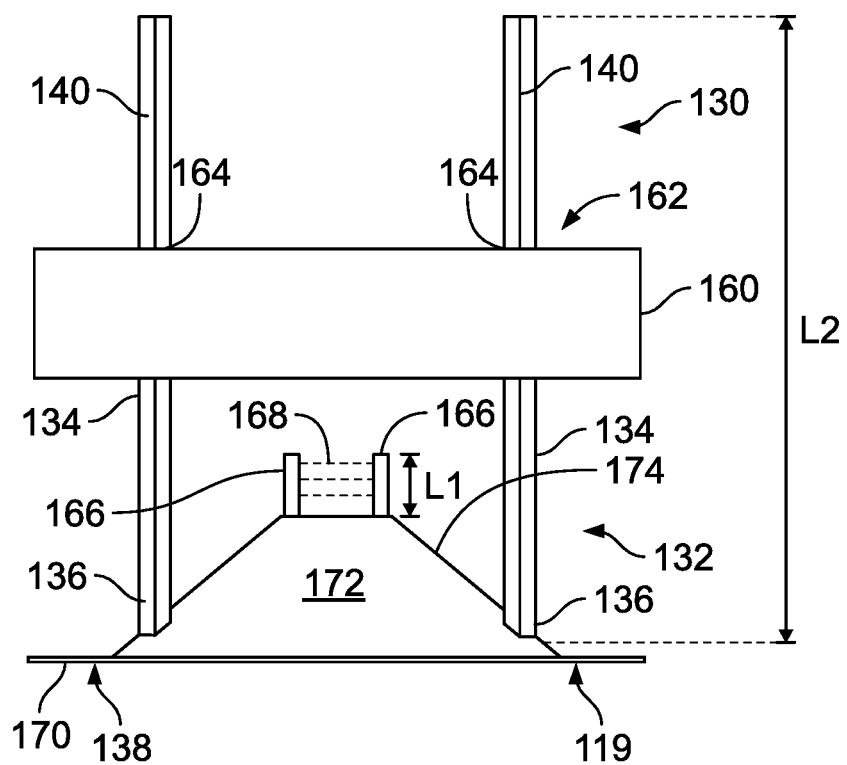
FIG. 8A is a side view of an adaptive electrode arrangement of the present disclosure according to another aspect of the present disclosure.
Figure 8B:
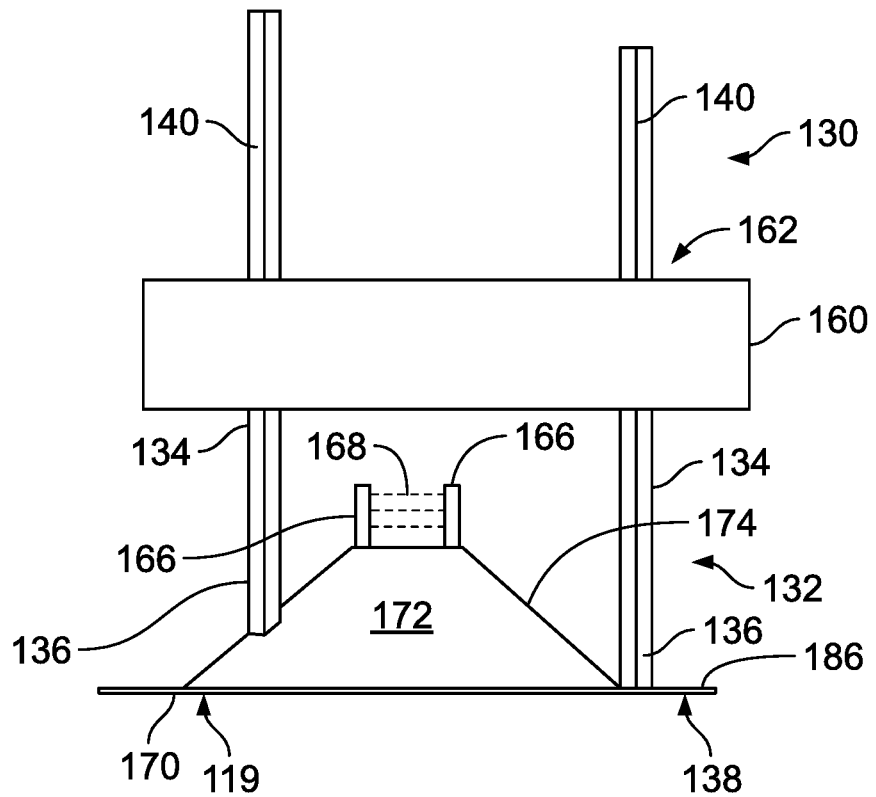
FIG. 8B is another side view of the adaptive electrode arrangement of FIG. 8A.
Figure 8C:
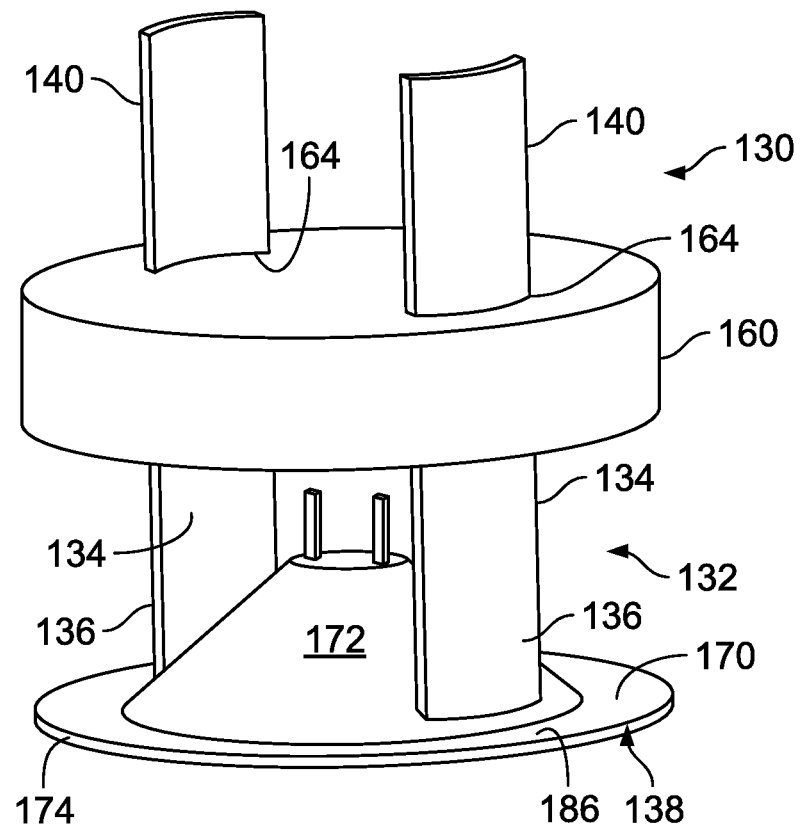
FIG. 8C is a perspective view of the adaptive electrode arrangement of FIG. 8A.

Referring now to FIGS. 8A-8C, an adaptive electrode arrangement 130 according to another aspect of the present disclosure is depicted. The adaptive electrode arrangement 130 may be used in the microwell plate assembly 10 of FIGS. 1-3. For example, one or more of the adaptive electrode arrangements 130 may alternatively form the arrays 20 of adaptive electrode arrangements of the microwell plate assembly 10. The adaptive electrode arrangement 130 is similar to the adaptive electrode arrangement 30 of FIG. 5, but also includes a cover plate, as described more below. Parts of the adaptive electrode arrangement 130 similar or identical to parts of the adaptive electrode arrangement 30 are numbered 100 more than the parts of the adaptive electrode arrangement 30. Likewise, parts of the adaptive electrode arrangement 130 different from the adaptive electrode arrangement 30 of FIGS. 5-7 include different reference numbers and are explained more below.

As depicted in FIG. 8A, and similar to the adaptive electrode arrangement 30 (FIG. 5), the adaptive electrode arrangement 130 is for introducing an electric field into the well 19 (FIG. 1) or a well 119, which is partially depicted in FIGS. 8A-8C. The adaptive electrode arrangement 130 includes a pair of electrodes 132 disposed within the well 19, 119. Each electrode 134 of the pair of electrodes 132 has a distal end 136 and a proximal end 140 and is independently and axially displaceable relative to each other and the bottom portion 138 of the well 19, 119. As a result, the distal end 136 of each electrode 134 is in contact, such as constant contact, with the bottom portion 138 of the well 19, 119, ensuring one or more of a uniform and constant or extended electric field is applied within the well 19, 119.

Unlike the adaptive electrode arrangement 30 of FIG. 5, the adaptive electrode arrangement 130 also includes a cover plate 160 having a pair of through-holes 162. Each through-hole 164 receives the proximal end 140 of each electrode 134 of the pair of electrodes 132. So configured, each electrode 134 is axially displaceable along an axis of the cover plate 160, allowing each electrode 134 to move or be moveable relative to one or more of the bottom portion 138 of the well 119 and the cover plate 160.

The well 119 partially depicted in FIGS. 8A-8C, for example, may include at least one micropost 166 having a length L1. In one example, and as depicted in FIGS. 8A-8C, the well 119 includes two microposts 166, each of which includes a length L1. In addition, each electrode 134 includes a length L2 that is either the same as or greater than (as depicted in FIG. 8A) the length L1 of the microposts 166. A microwire 168 is formed around the at least one micropost 166. Further, the well 119 may also include a bottom surface 170, a base 172 disposed on the bottom surface 170, and a ramp 174 to which the at least one micropost 166 may be attached. The ramp 174 may upwardly extend from the base 172 or be separate from the base 172. In this example, the bottom portion 138 may include one or more of the bottom surface 170, the base 172, and the ramp 174, such that the distal end 136 of each electrode 134 of the pair of electrodes 132 is in contact with one or more of the bottom surface 170, the base 172 or the ramp 174 of the well 119. In addition, the bottom portion 138 of the well 119 may be one or more of flat, convex or concave or any other geometric configuration. Each electrode 134 of the pair of electrodes 132 may move axially and independently of each other to maintain constant contact with the bottom portion 138 of the well 119, regardless of the geometric configuration of the well 119. While not depicted in FIGS. 1-3, the well 19 may also include each of the same features as the well 119 of FIGS. 8A-8C, for example, such as the microposts 166, the microwire 168, a bottom surface 170, a base 172 disposed on the bottom surface, and a ramp 174 to which the at least one micropost 166 may be attached.

For example, FIGS. 8A and 8C depict both distal ends 136 of each electrode 134 in contact with the ramp 174 of the well 119. FIG. 8B depicts one distal end 136 of one electrode 134 in contact with the ramp 174, while the other distal end 136 of the other electrode 134 is in contact with the bottom surface 170 of the well. More specifically, the configuration of the electrodes 134 in FIG. 8B depicts an example in which the electrodes 134 are inadvertently placed in a position offset from the ramp 174 of FIGS. 8A and 8C, for example. Because the electrodes 134 are axially moveable relative to each other and the cover plate 160, for example, the electrodes 134 automatically adapt to the different geometric surfaces of FIG. 8B due to the offset position, for example, and move downwardly toward the bottom portion 138 such that one electrode 134 is able to maintain contact with the ramp 174 and the other electrode 134 moves in a downward direction to contact the bottom surface 170. So configured, cells disposed between and near the electrodes 134, and not outside of the electrodes 134, such as on a fringe area 186 (FIGS. 8B, 8C) of the well 119, are stimulated by one or more of the uniform or extended electric field.

FIG. 8C further depicts an exemplary shape of the electrodes 134. More specifically, in one example, the electrodes 134 may be a partially cylindrical, curved, plate-like shape, as depicted in FIG. 8C. One of ordinary skill in the art will appreciate that the electrodes 134 may alternatively take the form of various other shapes, such as one or more of octagonal, hexagonal, rectangular, cylindrical, circular, semi-cylindrical, semi-circular, and/or triangular in shape and still fall within the scope of the present disclosure.

Figure 9:
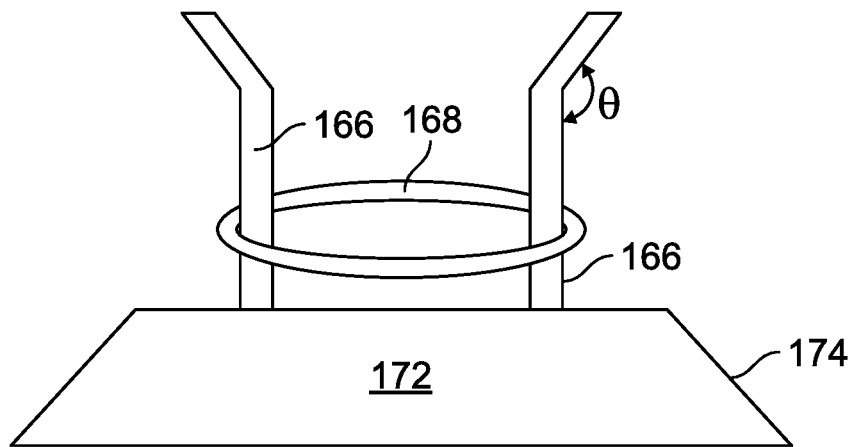
FIG. 9 is a side view of a portion of a well of a microwell plate assembly according to an aspect of the present disclosure.

Referring now to FIG. 9, a portion of a well of a microwell plate assembly is depicted, further illustrating several features of the well 119. More specifically, the well 119 includes two microposts 166 and a microwire 168 formed around the microposts 166. In this example, the microposts 166 include outwardly extending end portions at a proximal end of each micropost 166. One of ordinary skill in the art will appreciate that the microposts 166 may alternatively be various other shapes and configurations and still fall within the scope of the present disclosure. For example, the microposts 166 may alternatively be one or more of octagonal, hexagonal, rectangular, cylindrical, circular, semi-cylindrical, semi-circular and/or triangular in shape and still fall within the scope of the present disclosure. In this example, the microposts 166 are disposed on and attached to the base 172 of the well 119, which includes a ramp 174.

Figure 10A:
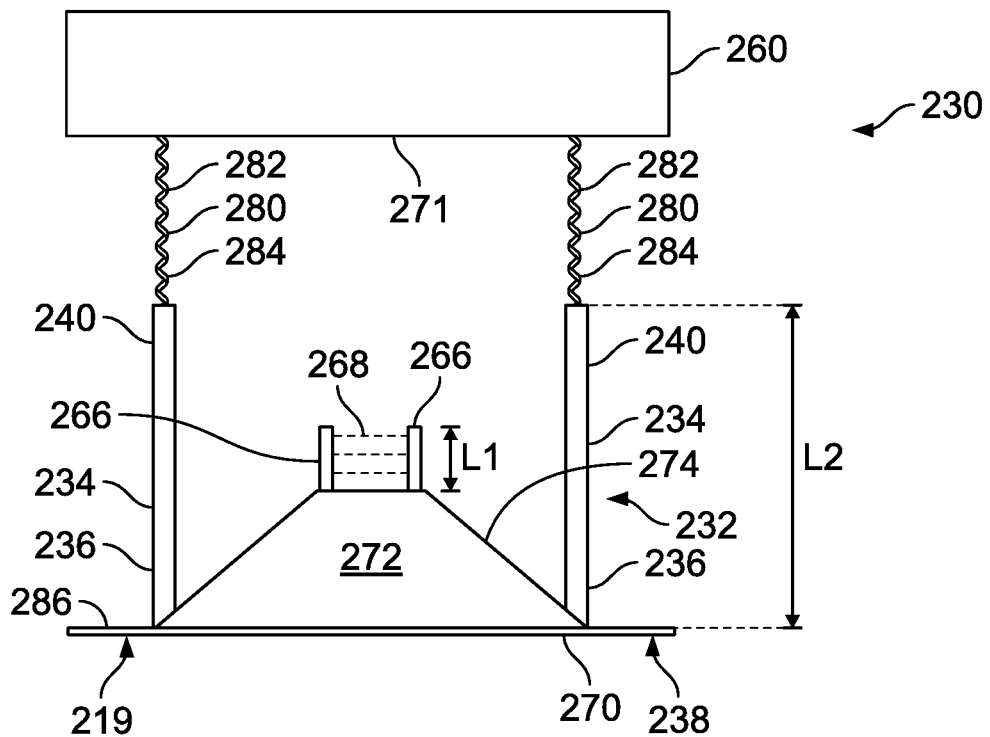
FIG. 10A is a side view of another adaptive electrode arrangement of the present disclosure according to another aspect of the present disclosure.
Figure 10B:
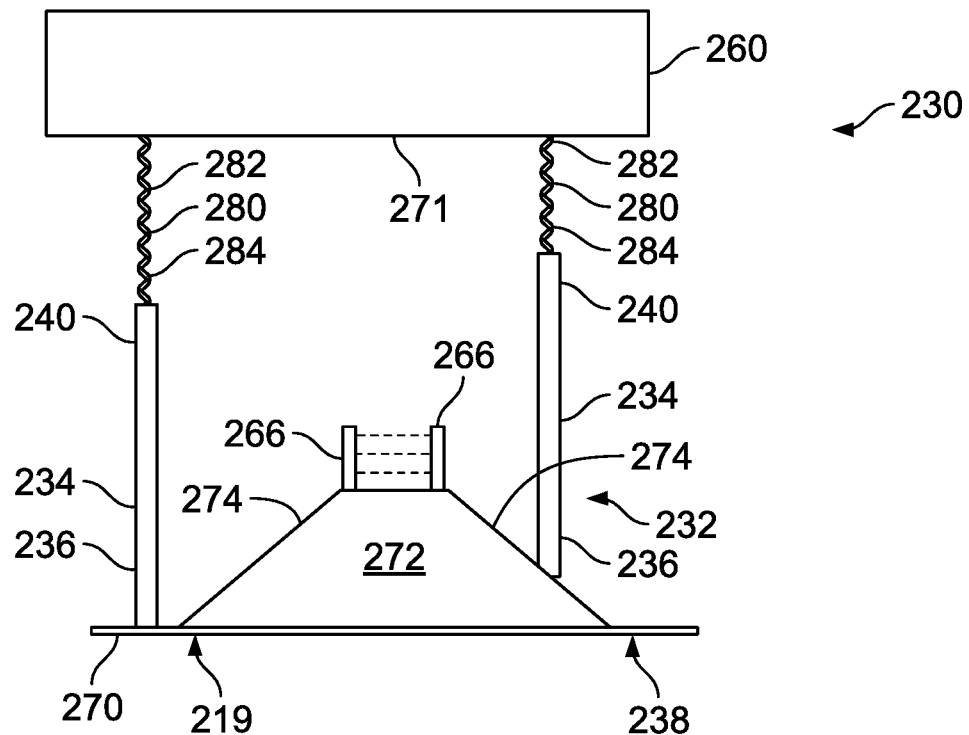
FIG. 10B is another side view of the adaptive electrode arrangement of FIG. 10A.
Figure 10C:
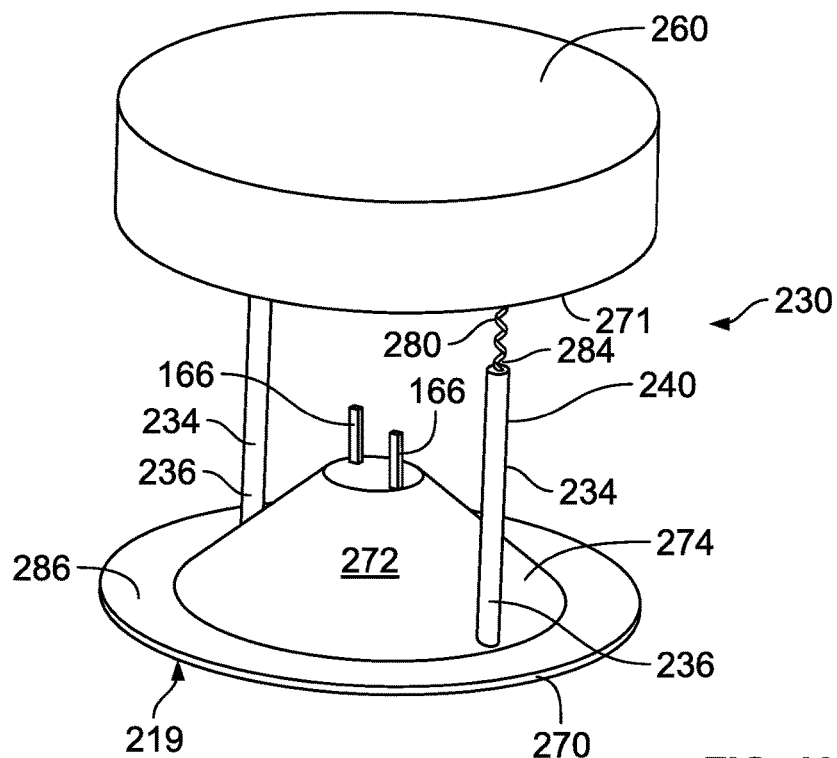
FIG. 10C is a perspective view of the adaptive electrode arrangement of FIG. 10A.

Referring now to FIGS. 10A-10C, an adaptive electrode arrangement 230 according to yet another aspect of the present disclosure is depicted. The adaptive electrode arrangement 230 may alternatively be used in the arrays 20 of adaptive electrode arrangements of the microwell plate assembly 10 of FIGS. 1-3 instead of the adaptive electrode arrangements 30, 130 for example. The adaptive electrode arrangement 230 is similar to the adaptive electrode arrangement 30 of FIG. 5, but also includes a cover plate and springs, as described more below. Parts of the adaptive electrode arrangement 230 of FIGS. 10A-10C that are similar or identical to parts of the adaptive electrode arrangement 30 are numbered 200 more than the parts of the adaptive electrode arrangement 30. Likewise, parts of the adaptive electrode arrangement 230 that are different from the adaptive electrode arrangement 30 of FIGS. 5-7 include different reference numbers and are explained more below.

As depicted in FIG. 10A, and similar to the adaptive electrode arrangements 30, 130, the adaptive electrode arrangement 230 is for introducing an electric field into the well 19 of FIG. 1, for example, or a well 219, which is partially depicted in FIGS. 10A-10B. The adaptive electrode arrangement 230 includes a pair of electrodes 232 adapted to be disposed within the well 219. Each electrode 234 of the pair of electrodes 232 has a distal end 236 and a proximal end 240 and is independently and axially displaceable relative to each other and the bottom portion 238 of the well 219. As a result, the distal end 236 of each electrode 234 is in contact, such as constant contact, with the bottom portion 238 of the well 219, ensuring one or more of a uniform and constant or extended electric field is applied within the well.

Like the adaptive electrode arrangement 130 of FIGS. 8A-8C, the adaptive electrode arrangement 230 also includes a cover plate 260 and a distal portion 271. A spring 280 having a first end 282 and a second end 284 attaches each electrode 234 to the cover plate 260. More specifically, the first end 282 of the spring 280 is attached to the distal portion 271 of the cover plate 260. The second end 284 of the spring 280 is attached to the proximal end 240 of one electrode 234 of the pair of electrodes 232. In a similar manner, another spring 280 has a first end 282 also attached to the distal portion 270 of the cover plate 260 and a second end 284 attached to the proximal end 240 of the other electrode 234 of the pair of electrodes 232. So configured, each electrode 234 is allowed to be axially displaceable relative to the cover plate 260, such as axially displaceable along an axis of the cover plate 260.

As noted, the well 219 is partially depicted in FIGS. 10A-10C, for example. Similar to wells 19, 119, the well 219 includes at least one micropost 266 having a length L1. In one example, the well 219 includes two microposts 266, each of which include a length L1. In addition, each electrode 234 includes a length L2 that is either the same as or greater than (as depicted in FIGS. 10A-10B) the length L1 of the microposts 266. Further, the well 219 may also include a bottom surface 270, a base 272 disposed on the bottom surface 270, and a ramp 274 to which the at least one micropost 266 may be attached. The ramp 274 may upwardly extend from the base 272 or be separate from the base 272. In this example, the bottom portion 238 may include one or more of the bottom surface 270, the base 272, and the ramp 274, such that the distal end 236 of each electrode 234 of the pair of electrodes 232 is in contact with one or more of the bottom surface 270, the base 272 or the ramp 274 of the well 219. In addition, the bottom portion 238 of the well 219 may be one or more of flat, convex or concave or any other geometric configuration. Each electrode 234 of the pair of electrodes 232 may move axially and independently of each other to maintain constant contact with the bottom portion 238 of the well 219, regardless of the geometric configuration of the well 219.

For example, FIG. 10A depicts the distal end 236 of one electrode 234 of the pair of electrodes 232 in contact with the ramp 274 of the well 219. The distal end 236 of the other electrode 234 of the pair of electrodes is also in contact with the ramp 274. In FIG. 10B, however, the pair of electrodes 232 of the adaptive electrode arrangement 230 are offset, such that the distal end 236 of the one electrode 234 is now in contact with the bottom surface 270 of the bottom portion 238 of the well 219. In addition, the distal end 236 of the other electrode 234 of the pair of electrodes 232 is still in contact with the ramp 274, but contacts the ramp 274 at a position closer to the micropost 266, for example. Because the electrodes 234 are axially moveable relative to each other and the cover plate 260, for example, via the springs 280, the electrodes 234 automatically adapt to the different geometric surfaces of the well 219 and move downwardly toward the bottom portion 238. As a result, one electrode 234 is able to maintain contact with the ramp 274, and the other electrode 234 moves in a downward direction to contact the bottom surface 270. So configured, cells disposed between the electrodes 234, and not outside of the electrodes 234, such as on a fringe area 286 (FIGS. 10A, 10C) of the well 119, are stimulated by one or more of the uniform or the extended electric field.

Figure 11:
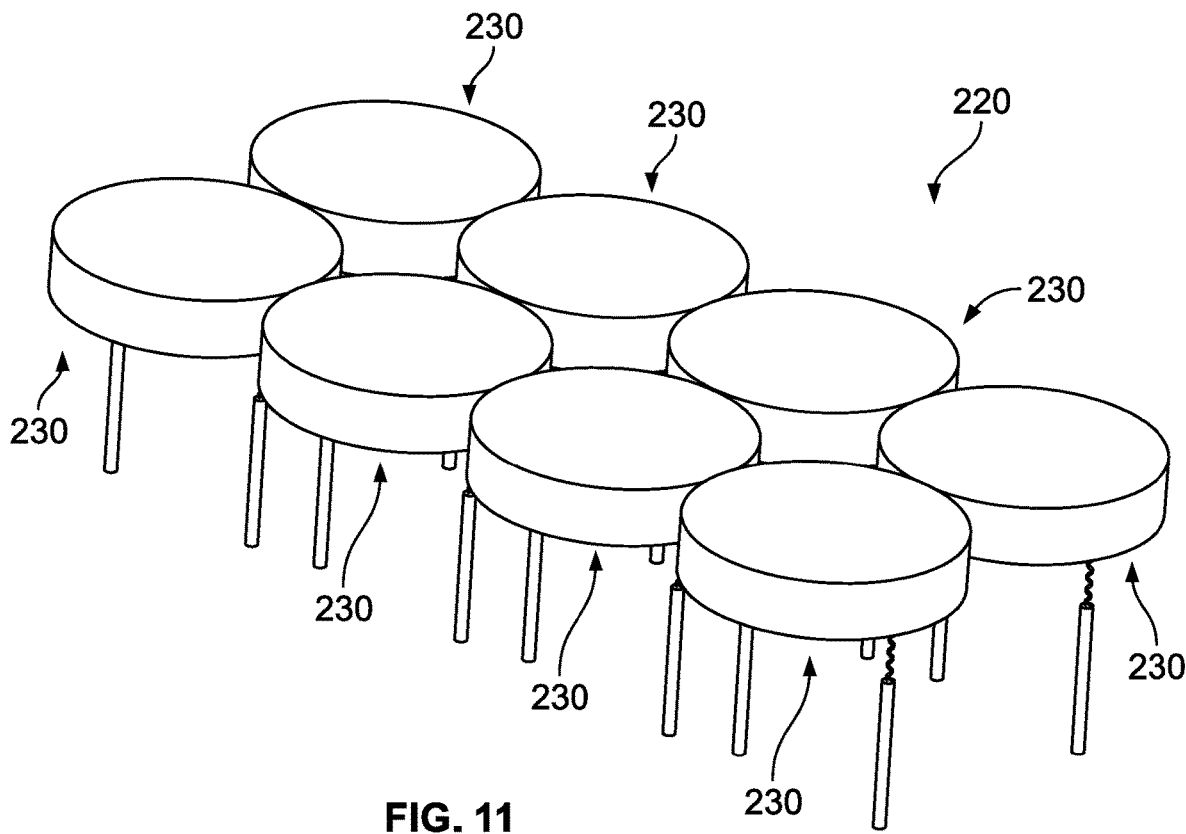
FIG. 11 is a perspective view of an array of adaptive electrode arrangements according to yet another aspect of the present disclosure.

Referring now to FIG. 11, another array 220 of adaptive electrode arrangements 230 is depicted. In this example, the array 220 includes eight adaptive electrode arrangements 230, each of which includes a pair of electrodes 232 attached to the cover plate 260, as explained relative to FIGS. 10A-10C, for example. While not depicted, the array 220 of the adaptive electrode arrangements 230 may be integrated into the microwell plate assembly 10 of FIGS. 1-3, for example, such as into the circuit board 22.

Figure 12:
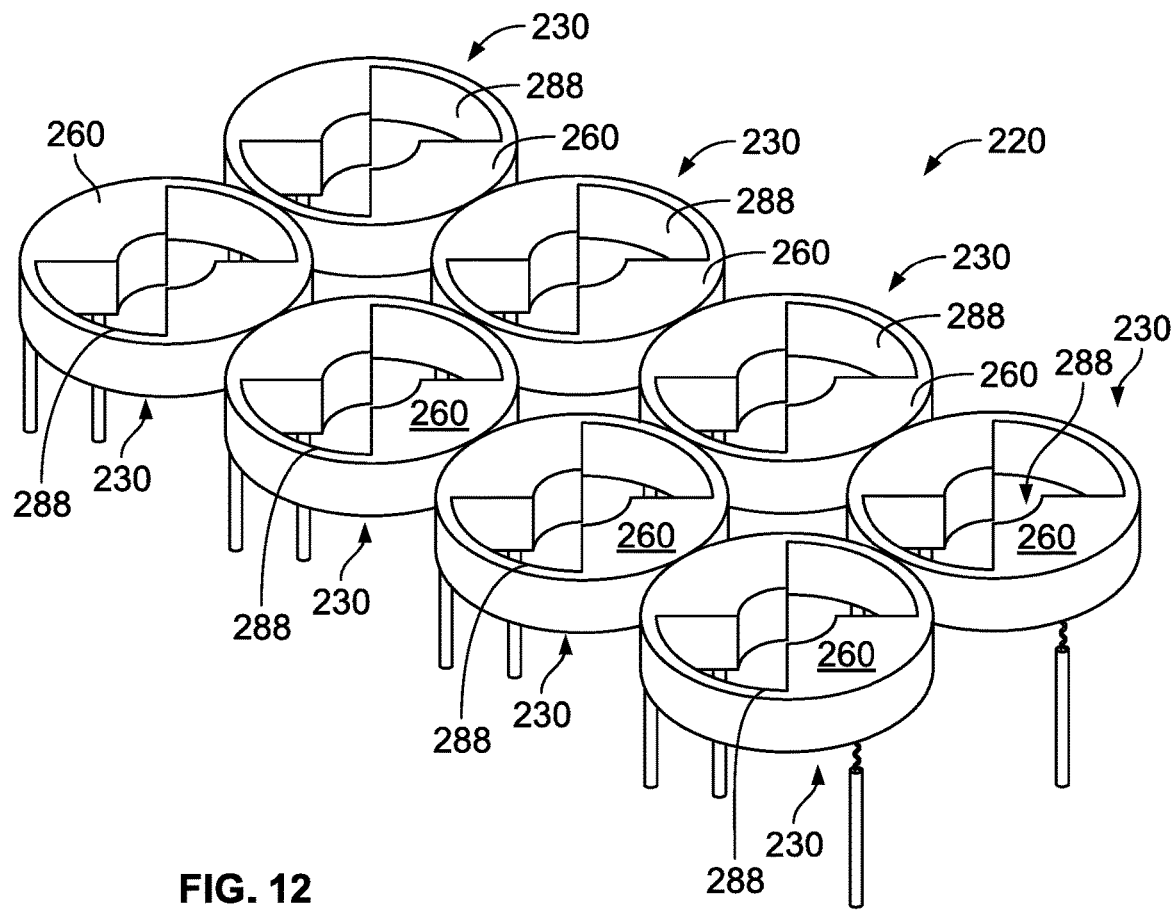
FIG. 12 is another perspective view of another array of adaptive electrode arrangements according to yet another aspect of the present disclosure.
Figure 13:
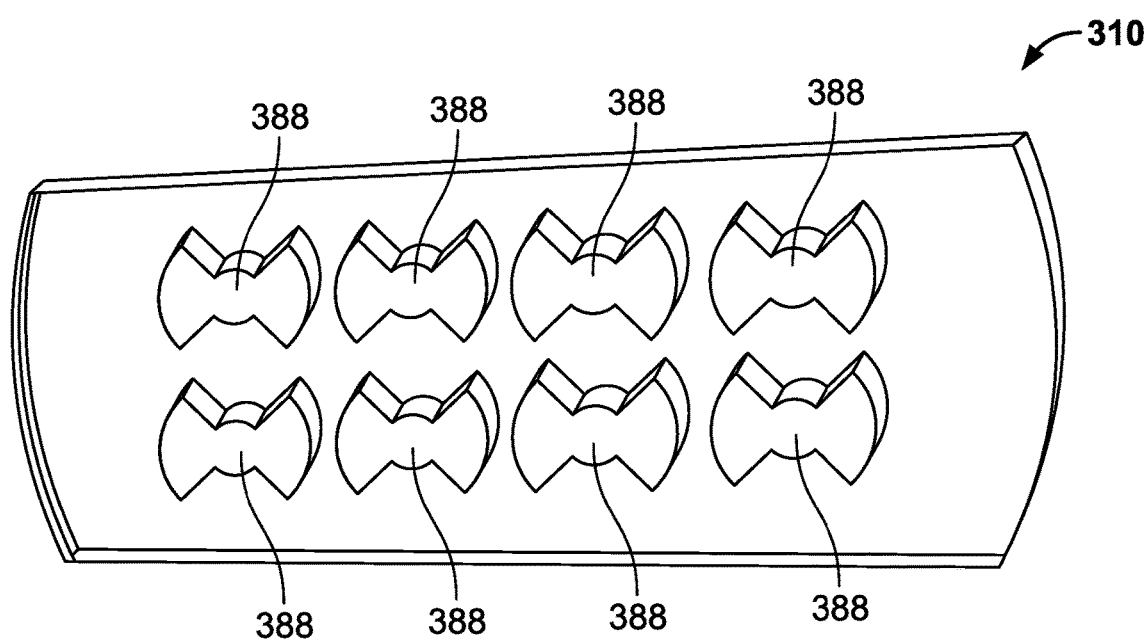
FIG. 13 is a top perspective view of a microwell electrode holder according to another aspect of the present disclosure.

Referring now to FIG. 12, the array 220 of the adaptive electrode arrangement 230 is again depicted. In this example, however, each cover plate 260 of each adaptive electrode arrangement 230 includes an opening 288. The opening 288 is disposed between the pair of electrodes 232 to allow for dispensing of solution within the well 19, 219, at any time, including while the electric field is being applied to the well 19, 219, for example. While the opening 288 is depicted as circular in part and semi-circular in part, the opening 288 may alternatively be various other shapes and sizes and still fall within the scope of the present disclosure. In addition, while the openings 288 are depicted in the array 220 of the adaptive electrode arrangement 230, the opening 288 may be included in a single adaptive electrode arrangement 230, such as any of the adaptive electrode arrangements depicted in FIGS. 10A-10C or FIGS. 8A-8C.

In yet another example, openings 388 may be formed in a microwell electrode holder 310 to which an array of adaptive electrode arrangements may be coupled. The openings 388 again allow for electrode insertion and solution dispensing at any time, including while an electric field is being applied to the well by the electrodes. Like the openings 288, the openings 388 may be any shape or combination of shapes and still fall within the scope of the present disclosure.

In view of the foregoing, one of ordinary skill in the art will appreciate the following example method 400 of introducing an electric field into a well 19, 119, 219. In one example, the method comprises disposing the pair of electrodes 32, 132, 232 within the well 19, 119, 219 of the microwell plate assembly 10, for example. The method further comprises independently and axially displacing each electrode 34, 134, 234 of the pair of electrodes 32, 132, 232 relative to each other to enable a distal end 36, 136, 236 of each electrode 34, 134, 234 to contact a bottom portion 38, 138, 238 of the well 19, 119, 219. The method also comprises maintaining constant contact of the distal end 36, 136, 236 of each electrode 34, 134, 234 of the pair of electrodes 32, 132, 232 with the bottom portion 38, 138, 238 and applying one or more of a uniform or extended electric field within the well 19, 119, 219.

In one example, the method 400 may further comprise providing a length of each electrode 34, 134, 234 of the pair of electrodes 32, 132, 232 that is at least about equal to or greater than a length of a micropost 166, 266 disposed in the well 19, 119, 219. In addition, independently and axially displacing each electrode 34, 134, 234 of the pair of electrodes 32, 132, 232 relative to each other may comprise providing one of at least one through-hole 28, 164 disposed within one of the circuit board 22 or the cover plate 160 for receiving a proximal end 40, 140 of each electrode 34, 134, 234 of the pair of electrodes 32, 132, 232, or at least one spring 42, 280 for coupling the proximal end 40, 240 of each electrode 34, 234 to one of the circuit board 22 or the cover plate 260. Further, maintaining constant contact of a distal end 36, 136, 236 of each electrode 34, 134, 234 of the pair of electrodes 32, 132, 232 with the bottom portion 38, 138, 238 of the well 19, 119, 219 may comprise providing at least one through-hole 164 within a cover plate 160 for receiving a proximal end 140 of each electrode 134 or at least one spring 280 having a first end 282 attached to the cover plate 260 and a second end 284 attached to the proximal end 240 of each electrode 234 of the pair of electrodes 232. This allows the distal end 136, 236 of each electrode 134, 234 to move relative to the cover plate 160, 260 and each other to accommodate different heights and/or geometric configurations of the bottom portion 38, 138, 238 of the well 19, 119, 219.

In another example, the method 400 may further comprise integrating a pair of electrodes 32, 132, 232 into the circuit board 22 of a microwell plate assembly 10 by one or more of at least one spring 42 or at least one through-hole 26 disposed within the circuit board 22. The pair of electrodes 32, 132, 232 may be disposed within the well 19 before or after being disposed within the circuit board. In addition, the method 400 may further comprise providing an array 20 of adaptive electrode arrangements 30, 130, 230, each adaptive electrode arrangement 30, 130, 230 having a pair of electrodes 32, 132, 232, and controlling stimulation inputs by wiring the pairs of electrodes 32, 132, 232 in parallel or in series to multiple pulse generators and amplifiers through the circuit board 22. The method 400 may also further comprise dispensing solution through at least one opening 28, 288, 388 disposed in one or more of a circuit board 22 of a microwell plate assembly 10 or a cover plate 160, 260 coupled to the pair of electrodes 32, 132, 232, while simultaneously applying the electric field within the well 19, 119, 219 of the plurality of wells.

In one example, maintaining constant contact of the distal end 36, 136, 236 of each electrode 34, 134, 234 of the pair of electrodes 32, 132, 232 within the bottom portion 38, 138, 238 of the well 19, 119, 219 may include preventing cells adapted to be disposed within the well 19, 119, 219 from being stimulated by a fringe of the electric field. More specifically, and as described above relative to FIG. 1B (B), conventional fixed height electrodes do not always contact the bottom portion of the well, resulting in cells at the bottom of the well being disposed below the fixed height electrodes and, thus, stimulated by a fringe of the electric field of the electrodes, which is a non-uniform electric field, for example. Using adaptive electrodes allows the distal ends 36, 136, 236 of each electrode 34, 134, 234 to maintain constant contact with the bottom portion of the well 19, 119, 219, such that cells on the bottom portion of the well 19, 119, 219 are typically disposed between the electrodes 34, 134, 234 and, thus, stimulated by a uniform electric field of the adaptive electrodes 34, 134, 234, and not a fringe of an electric field. 6Additionally or alternatively, maintaining constant contact of the distal end 36, 136, 236 of each electrode 34, 134, 234 of the pair of electrodes 32, 132, 232 within the bottom portion 38, 138, 238 of the well 19, 119, 219 may comprise maintaining constant contact of the distal end 36, 136, 236 of each electrode 34, 134, 234 with the bottom portion 38, 138, 238 regardless of a depth of different areas of the bottom portion 38, 138, 238 of the well 19, 119, 219.

Further, in another example, independently and axially displacing each electrode 34, 134, 234 of the pair of electrodes 32, 132, 232 relative to each other to enable a distal end 36, 136, 236 of each electrode 34, 134, 234 of the pair of electrodes 32, 132, 232 to contact a bottom portion 38, 138, 238 of the well 19, 119, 219 may comprise displacing the distal end 36, 136, 236 of a first electrode 34, 134, 234 of the pair of electrodes 32, 132, 232 to be in contact with the bottom portion 38, 138, 238 of the well 19, 119, 219 at one of a lower depth than, a same depth as, or a higher depth than a distal end 36, 136, 236 of the second electrode 34, 134, 234 of the pair of electrodes 32, 132, 232 in contact with the bottom portion 38, 138, 238 of the well 19, 119, 219. The bottom portion 38, 138, 238 of the well 19, 119, 219 may include one of a bottom surface 170, 270 of the well, a ramp 174, 274 disposed within the well, or a base 172, 272 disposed in the well 119, 219.

Still further, in one example, the well may further comprise a cell, and the cell may be a mammalian cell. The mammalian cell may comprise one of a pluripotent stem cell or a cardiomyocyte.

In another example, one of ordinary skill in the art will further appreciate the following method 500 of synchronizing a behavior of a population of cells by introducing an electric field into a well 19, 119, 219 of a microwell plate assembly 10. The method 500 comprises adding the population of cells in the well 19, 119, 219 and disposing a pair of electrodes 32, 132, 232 within the well 19, 119, 219. The method 500 further comprises independently and axially displacing each electrode 34, 134, 234 of the pair of electrodes 32, 132, 232 relative to each other to enable a distal end 36, 136, 236 of each electrode 34, 134, 234 of the pair of electrodes 32, 132, 232 to contact a bottom portion 38, 138, 238 of the well 19, 119, 219. The method 500 further comprises maintaining constant contact of the distal end 36, 136, 236 of each electrode 34, 134, 234 of the pair of electrodes 32, 132, 232 with the bottom portion 38, 138, 238 of the well 19, 119, 219. In addition, the method 500 further comprises applying a uniform electric field within the well 19, 119, 219, such that the behavior of each cell of the population of cells is approximately synchronized.

In yet another example, one of ordinary skill in the art will also appreciate the following method 600 of altering a membrane potential of a cell by introducing an electric field into a well of a microwell plate assembly. The method 600 comprises adding a cell in a well 19, 119, 219 of the microwell plate assembly 10 and disposing a pair of electrodes 32, 132, 232 within the well 19, 119, 219. The method 600 also includes independently and axially displacing each electrode 34, 134, 234 of the pair of electrodes 32, 132, 232 relative to each other to enable a distal end 36, 136, 236 of each electrode 34, 134, 234 of the pair of electrodes 32, 132, 232 to contact a bottom portion 38, 138, 238 of the well 19, 119, 219. The method 600 further includes maintaining constant contact of the distal end 36, 136, 236 of each electrode 34, 134, 234 of the pair of electrodes 32, 132, 232 with the bottom portion 38, 138, 238 of the well 19, 119, 219 and applying a uniform and/or extended electric field within the well 19, 119, 219, such that the membrane potential of the cell is excited.

In both example methods 500 and 600, for example, the population of cells may comprise pluripotent cells. In another example, the behavior of the pluripotent cells after applying the uniform electric field is to further differentiate, and the pluripotent cells may differentiate into cardiomyocytes. In addition, the differentiated pluripotent cells may exhibit at least one mature characteristic, and the cardiomyocytes may exhibit at least one mature cardiomyocyte-like characteristic, as is known and understood by persons having ordinary skill in the art. Further, the population of cells may comprise cardiomyocytes, and the behavior of the cardiomyocytes after applying the uniform electric field may be beating. In yet another example, the method 500 may further comprise culturing the population of cells.

One of ordinary skill in the art will appreciate the following advantages of the adaptive electrode arrangements 30, 130, 230 and methods 400, 500, 600 described above. For example, the adaptive electrode arrangements 30, 130, 230 and the foregoing related methods eliminate the need to precisely measure the depth of a well to understand how deep the electrodes must be lowered into the well to affect a uniform electric field across the cells. In addition, because the electrodes 34, 134, 234 are able to be in contact with the bottom portion 38, 138, 238 of the well 19, 119, 219 regardless of the depth or various geometric configurations of the well 19, 119, 219, cells are disposed between the electrodes 34, 134, 234 and not below or outside of the electrodes 34, 134, 234, such as on the fringe area 186 (FIGS. 8B, 8C), 286 (FIGS. 10A, 10C) of the well 119, 219 outside of the uniform electric field being applied. So configured, the cells are prevented from being stimulated by a fringe of the electric field (a non-uniform electric field) being applied, for example. As a result, all cells added to the well 19, 119, 219, receive the desired external pacing and ultimately are able to resemble an in vivo physiological behavior. Further, the openings 28 in the circuit board 22, for example, and the openings 288, e.g., cut-outs, in the cover plates 160, 260 enable reagent dispensing or solution to be injected into the well while simultaneously conducting the electrical stimulation of the cells, a feature conventional electrode arrangements are not capable of doing.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

As used herein, "synchronize," "synchronizing" and the like refers in the context of a cell population to coordinate cells in a selected cell behavior (such as the beating of cardiomyocytes) such that the individual cells behave in approximately the same way at approximately the same time.

The term "pluripotent" refers to a cell that can give rise to any type of cell in the body except germ line cells. The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages. Pluripotency is also evidenced by the expression of embryonic stem (ES) cell markers, although the preferred test for pluripotency is the demonstration of the capacity to differentiate into cells of all three germ layers, as detected using, for example, a nude mouse teratoma formation assay. Pluripotent cells can undergo further differentiation into multipotent cells that are committed to give rise to cells that have a particular function. For example, multipotent cardiovascular cells, or cardiac progenitor cells, can give rise to the cells of the heart, including cardiomyocytes, as well as other cells involved in the vasculature of the heart.

The term "phenotype" refers to one or a number of total biological characteristics that define the cell or organism under a particular set of environmental conditions and factors, regardless of the actual genotype.

In the context of cell ontogeny, the term "differentiated" or "differentiating" is a relative term. A "differentiated cell" is a cell that has progressed further down the developmental pathway than its precursor. Thus, stem cells can differentiate to lineage-restricted precursor cells (such as a mesodermal stem cell), which in turn can differentiate into other types of precursor cells further down the pathway (such as an atrial precursor), and then to an end-stage differentiated cell, such as atrial cardiomyocytes or smooth muscle cells, which play a characteristic role in a certain tissue type, and may or may not retain the capacity to proliferate further. The term "differentiated cell" refers to any primary cell that is not, in its native form, pluripotent as that term is defined herein. The term a "differentiated cell" also encompasses cells that are partially differentiated, such as multipotent cells, or cells that are stable non-pluripotent partially reprogrammed cells. In some cases, a differentiated cell is a cell that is a stable intermediate cell, such as a non-pluripotent partially reprogrammed cell.

The term "differentiation" refers to the process whereby a cell moves further down the developmental pathway and begins expressing markers and phenotypic characteristics known to be associated with a cell that are more specialized and closer to becoming terminally differentiated cells. The pathway along which cells progress from a less committed cell to a cell that is increasingly committed to a particular cell type, and eventually to a terminally differentiated cell, is referred to as progressive differentiation or progressive commitment. Cells which are more specialized (e.g., have begun to progress along a path of progressive differentiation) but not yet terminally differentiated are referred to as partially differentiated. Differentiation is a developmental process whereby cells assume a more specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, in the context of this specification, the terms "differentiation" or "differentiated" refer to cells that are more specialized in their fate or function than at one time in their development. For example, a differentiated cell includes a cardiomyocyte which has differentiated from a cardiac progenitor cell, where such cardiac progenitor cells can in some instances be derived from the differentiation of an embryonic stem cell, or alternatively from the differentiation of an induced pluripotent stem (iPS) cell, or in some embodiments from a human embryonic stem cell line. A cell that is "differentiated" relative to a progenitor cell has one or more phenotypic differences relative to that progenitor cell and characteristics of a more mature or specialized cell type. Phenotypic differences include, but are not limited to, morphologic differences and differences in gene expression and biological activity, including not only the presence or absence of an expressed marker, but also differences in the amount of a marker and differences in the co-expression patterns of a set of markers.

For example, cardiomyocytes and precursor cells derived from pluripotent stem cell lines often have morphological characteristics of cardiomyocytes from other sources. They can be spindle, round, triangular or multi-angular shaped, and they may show striations characteristic of sarcomeric structures detectable by, for example, immunostaining. They may form flattened sheets of cells, or aggregates that stay attached to the substrate or float in suspension, showing typical sarcomeres and atrial granules when examined by electron microscopy.

Pluripotent stem cell-derived cardiomyocytes and their precursors typically have at least one of the following Cardiomyocyte specific markers:

Cardiac troponin T (cTnT), a subunit of troponin complex that provides a calcium-sensitive molecular switch for the regulation of striated muscle contraction.

Cardiac troponin T (cTnT), plays an important role in fixing the troponin complex on actin filaments, organizes the troponin subunits in the troponin complex, and also participates in the regulation of muscle contraction.

Nkx2.5, a cardiac transcription factor expressed in cardiac mesoderm during early mouse embryonic development, which persists in the developing heart.

Cardiomyocytes also typically express at least one (and often at least 3, 5, or more) of the following markers:

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

Myosin heavy chain (MHC), particularly the P3 chain which is cardiac-specific.

Titin, tropomyosin, α-sarcomeric actinin, and desmin.

GATA-4, a transcription factor that is highly expressed in cardiac mesoderm and persists in the developing heart. It regulates many cardiac genes and plays a role in cardiogenesis.

MEF-2A, MEF-2B, MEF-2C, and MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (. β1-AR)

Creatine kinase MB (CK-MB) and myoglobin, which are elevated in serum following myocardial infarction α-cardiac actin, early growth response-I, and cyclin D2.

Further phenotypic characteristics of maturing cardiomyocytes include a rate of contraction that decreases with differentiation and maturation in culture, as in normal mouse development. Cardiomyocyte differentiation can be divided into three developmental stages: (1) early (pacemaker-like or primary myocardial-like cells); (2) intermediate; and (3) terminal (atrial-, ventricular-, nodal-, His, and Purkinje-like cells). In the early stages, the nascent myofibrils are sparse and irregular but myofibrillar and sarcomeric organization increases with maturation. Functional gap junctions develop between cells. Likewise, the electrophysiological properties of differentiating cardiomyocytes develop with differentiation in a manner reminiscent of their development in embryogenesis. Furthermore, electrophysiologically, three major types of cardiomyocytes can arise: those with atrial, nodal-, and ventricular-like electrophysiological phenotypes.

EMBODIMENTS

1. A well for electrically stimulating at least one cell, the well having a bottom portion and comprising:

an adaptive electrode arrangement for introducing an electric field into the well, the adaptive electrode arrangement including:

a pair of electrodes disposed within the well, the pair of electrodes having a distal end and independently and axially displaceable relative to each other and the bottom portion of the well;

wherein the distal end of each electrode of the pair of electrodes is in contact with the bottom portion of the well, ensuring one or more of a uniform or extended electric field is applied within the well.

2. The well of embodiment 1, further comprising one or more of at least one micropost, a microwire formed around the at least one micropost, a bottom surface, a base disposed on the bottom surface, and a ramp, one of extending or separate from the base, to which the at least one micropost is attached, the bottom portion including one or more of the bottom surface, the base, and the ramp, such that the distal end of each electrode of the pair of electrodes is in contact with one of the bottom surface, the base, or the ramp of the well.

3. The well of any one of embodiments 1-2, the well further comprising at least one micropost having a length, and each electrode of the pair of electrodes includes a length that is at least about the same or greater than the length of the at least one micropost.

4. The well of any one of embodiments 1-3, wherein the adaptive electrode arrangement is adapted to be integrated to a circuit board, the circuit board including a plurality of openings and a through-hole disposed on either side of each opening, the through-hole for receiving a proximal end of each electrode of the pair of electrodes.

5. The well of any one of embodiments 1-4, further comprising a spring for securing each proximal end of each electrode of the pair of electrodes to the circuit board and enabling each electrode to be independently and axially displaceable, wherein each electrode of the pair of electrodes is disposed on either side of an opening of the plurality of openings of the circuit board.

6. The well of any one of embodiments 1-5, wherein the bottom portion of the well is one or more of flat, convex or concave.

7. The well of any one of embodiments 1-3, wherein the adaptive electrode arrangement further includes a cover plate having a pair of through-holes, each through-hole for receiving a proximal end of each electrode of the pair of electrodes, and each electrode axially displaceable along an axis of the cover plate, allowing each electrode to move relative to one or more of the bottom portion of the well and the cover plate.

8. The well of any one of embodiments 1-3, wherein the adaptive electrode arrangement further includes a cover plate having a distal portion, each electrode of the pair of electrodes having a proximal end, and the adaptive electrode arrangement further comprising a spring with a first end attached to the distal portion of the cover plate and a second end coupled to the proximal end of each electrode of the pair of electrodes to couple each electrode to the cover plate, allowing each electrode to be axially displaceable along an axis of the cover plate.

9. The well of any one of embodiments 7-8, wherein the distal end of each electrode of the pair of electrodes is in constant contact with the bottom portion of the well, the bottom portion of the well including one or more of a bottom surface, a base, or a ramp of the well.

10. The well of any one of embodiments 7-9, wherein each cover plate includes an opening disposed between the pair of electrodes to allow for dispensing of solution within the well while the electric field is being applied within the well.

11. A microwell plate assembly comprising:
a microwell plate having a plurality of wells, each well of the plurality of wells having a bottom portion; and
an array of adaptive electrode arrangements for introducing an electric field into each well of the plurality of wells, each adaptive electrode arrangement including:
a pair of electrodes disposed within the well of the plurality of wells, each electrode of the pair of electrodes having a distal end and independently and axially displaceable relative to each other and the bottom portion of the well;
wherein the distal end of each electrode of the pair of electrodes is in contact with the bottom portion of the well, ensuring a uniform and constant electric field is applied within the well.

12. The assembly of embodiment 11, the well further comprising one or more of at least one micropost, a microwire formed around the at least one micropost, a bottom surface, a base disposed on the bottom surface, and a ramp, one of extending or separate from the base, to which the at least one micropost is attached, the bottom portion including one or more of the bottom surface, the base, and the ramp, such that the distal end of each electrode of the pair of electrodes is in contact with one of the bottom surface, the base, or the ramp of the well, and the bottom portion of the well is one or more of flat, convex or concave.

13. The assembly of any one of embodiments 11-12, the well further comprising at least one micropost having a length, and each electrode of the pair of electrodes includes a length that is at least about the same or greater than the length of the at least one micropost.

14. The assembly of any one of embodiments 11-13, further comprising a circuit board to which the array of adaptive electrode arrangements is integrated, the circuit board including a plurality of openings and a through-hole disposed on either side of each opening, the through-hole for receiving a proximal end of each electrode of the pair of electrodes.

15. The assembly of any one of embodiments 11-14, further comprising a first spring having a first portion and a second portion, the first portion coupled to a proximal end of a first electrode disposed on a first side of the circuit board, and the second portion coupled to a proximal end of a second electrode disposed on the first side of the circuit board, the spring for securing the first and second electrodes to the circuit board and enabling axial displacement of the first and second electrodes.

16. The assembly of embodiment 15, further comprising a second spring having a first portion and a second portion, the first portion coupled to a proximal end of a third electrode disposed on a second side of the circuit board opposite the first electrode, and the second portion coupled to a proximal end of a fourth electrode disposed on the second side of the circuit board opposite the second electrode, the spring for securing the third and fourth electrodes to the circuit board and enabling axial displacement of the third and fourth electrodes, such that the first and third electrodes are disposed on either side of a first opening of the plurality of openings of the circuit board and the second and fourth electrodes are disposed on either side of a second opening of the plurality of openings of the circuit board.

17. The assembly of embodiment 16, wherein the first and third electrodes form a pair of electrodes of a first adaptive electrode arrangement of the array of adaptive electrode arrangements, and the second and fourth electrodes form a pair of electrodes of a second adaptive electrode arrangement of the array of adaptive electrode arrangements.

18. The assembly of any one of embodiments 14-17, wherein the circuit board has a configuration selected from the group consisting of:
(a) at least one section, each section including multiple arrays of adaptive electrode arrangements, each array of adaptive electrode arrangements including multiple adaptive electrode arrangements; or
(b) a single unibody, the unibody including multiple arrays of adaptive electrode arrangements, each array of adaptive electrode arrangements including multiple adaptive electrode arrangements.

19. The assembly of any one of embodiments 14-17, where in the printed circuit board includes three sections, each section including four arrays of adaptive electrode arrangements, each array of adaptive electrode arrangements including eight adaptive electrode arrangements.

20. The assembly of any one of embodiments 11-13, wherein each adaptive electrode arrangement further includes a cover plate having a pair of through-holes, each through-hole for receiving a proximal end of each electrode of the pair of electrodes, and each electrode axially displaceable along an axis of the cover plate, allowing each electrode to move relative to one or more of the bottom portion of the well and the cover plate.

21. The assembly of any one of embodiments 11-13, wherein each adaptive electrode arrangement further includes a cover plate having a distal portion, each electrode of the pair of electrodes having a proximal end, and the adaptive electrode arrangement further comprising a spring with a first end attached to the distal portion of the cover plate and a second end coupled to the proximal end of each electrode of the pair of electrodes to couple each electrode to the cover plate, allowing each electrode to be axially displaceable along an axis of the cover plate.

22. The assembly of any one of embodiments 20-21, wherein the distal end of each electrode of the pair of electrodes is in constant contact with the bottom portion of the well, the bottom portion of the well including one or more of a bottom surface, a base, or a ramp of the well, and the bottom portion of the well is one or more of flat, convex or concave.

23. The assembly of any one of embodiments 20-22, wherein each cover plate includes an opening disposed between the pair of electrodes to allow for dispensing of solution within the well while the electric field is being applied within the well.

24. An adaptive electrode arrangement for a microwell plate, the adaptive electrode arrangement comprising:
one of a circuit board or a cover plate; and
a pair of electrodes coupled to one of the circuit board or the cover plate and adapted to be disposed within a well of a plurality of wells, the pair of electrodes independently and axially displaceable relative to a bottom portion of the well and each other, each electrode of the pair of electrodes having a distal end;
wherein the distal end of each electrode of the pair of electrodes is adapted to be in constant contact with the bottom portion of the well when disposed within the well, ensuring a uniform and constant electric field is applied within the well.

25. The adaptive electrode arrangement of embodiment 24, comprising the circuit board, wherein the circuit board includes an opening for enabling solution to be introduced into the well and a through-hole disposed on either side of each opening, the through-hole for receiving a proximal end of each electrode of the pair of electrodes.

26. The adaptive electrode arrangement of any one of embodiments 24-25, further comprising a spring for securing each proximal end of each electrode of the pair of electrodes to the circuit board and enabling each electrode to be independently and axially displaceable.

27. The adaptive electrode arrangement of embodiment 24, comprising the cover plate, wherein the cover plate includes a pair of through-holes, each through-hole for receiving a proximal end of each electrode of the pair of electrodes, and each electrode axially displaceable along an axis of the cover plate, allowing each electrode to move relative to a bottom portion of the well of the plurality of wells.

28. The adaptive electrode arrangement of embodiment 24, comprising the cover plate, wherein the cover plate includes a distal portion and a spring with a first end attached to the distal portion of the cover plate and a second end attached to a proximal end of each electrode of the pair of electrodes, allowing each electrode to be axially displaceable along an axis of the cover plate.

29. The adaptive electrode arrangement of any one of embodiments 24-28, wherein the distal end of each electrode of the pair of electrodes is adapted to be in constant contact with one or more of a bottom portion, a bottom surface, a base, or a ramp of the well, and the bottom portion of the well is one or more of flat, convex or concave.

30. The adaptive electrode arrangement of any one of embodiments 27-29, wherein each cover plate includes an opening disposed between the pair of electrodes to allow for dispensing of solution within the well while the electric field is being applied within the well.

31. A method of introducing an electric field into a well, the method comprising:
disposing a pair of electrodes within the well;
independently and axially displacing each electrode of the pair of electrodes relative to each other to enable a distal end of each electrode of the pair of electrodes to contact a bottom portion of the well;
maintaining constant contact of the distal end of each electrode of the pair of electrodes with the bottom portion of the well; and
applying a uniform electric field within the well.

32. The method of embodiment 31, further comprising providing a length of each electrode of the pair of electrodes that is at least about equal to or greater than a length of a micropost disposed in the well.

33. The method of any one of embodiments 31-32, wherein independently and axially displacing each electrode of the pair of electrodes relative to each other comprises providing one of at least one through-hole disposed within one of a lid or a cover plate for receiving a proximal end of each electrode of the pair of electrodes, or at least one spring for coupling the proximal end of each electrode to one of a lid or a cover plate.

34. The method of any one of embodiments 31-33, wherein maintaining constant contact of a distal end of each electrode of the pair of electrodes with the bottom portion of the well comprises providing at least one through-hole within a cover plate for receiving a proximal end of each electrode or at least one spring having a first end attached to the cover plate and a second end attached to the proximal end of each electrode of the pair of electrodes, allowing the distal end of each electrode to move relative to the cover plate and each other to accommodate different heights and/or geometric configurations of the bottom portion of the well.

35. The method of any one of embodiments 31-33, further comprising integrating a pair of electrodes into a circuit board of a microwell plate assembly by one or more of at least one spring or at least one through-hole disposed within the circuit board before disposing the pair of electrodes within the well.

36. The method of embodiment 35, further comprising providing an array of adaptive electrode arrangements, each adaptive electrode arrangement having a pair of electrodes and the well is one well of a plurality of wells of a microwell plate assembly, and controlling stimulation inputs by wiring the pairs of electrodes in parallel or in series to one or multiple pulse generators and amplifiers through the circuit board.

37. The method of any one of embodiments 31-36, further comprising dispensing solution through at least one opening disposed in one or more of a circuit board of a microwell plate assembly or a cover plate coupled to the pair of electrodes while simultaneously applying the electric field within the well of the plurality of wells.

38. The method of any one of embodiments 31-37, wherein maintaining constant contact of the distal end of each electrode of the pair of electrodes within the bottom portion of the well includes preventing cells adapted to be disposed within the well from being stimulated by a fringe of an electric field.

39. The method of any one of embodiments 31-38, wherein maintaining constant contact of the distal end of each electrode of the pair of electrodes within the bottom portion of the well comprises maintaining constant contact of the distal end of each electrode with the bottom portion regardless of a depth of different areas of the bottom portion of the well.

40. The method of any one of embodiments 31-39, wherein independently and axially displacing each electrode of the pair of electrodes relative to each other to enable a distal end of each electrode of the pair of electrodes to contact a bottom portion of the well comprises displacing a distal end of a first electrode of the pair of electrodes to be in contact with the bottom portion of the well at one of a lower depth than, a same depth as, or a higher depth than a distal end of the second electrode of the pair of electrodes in contact with the bottom portion of the well, the bottom portion of the well including one of a bottom surface of the well, a ramp disposed within the well, or a base disposed in the well.

41. The method of any one of embodiments 31-40, wherein the well further comprises a cell.

42. The method of embodiment 41, wherein the cell is a mammalian cell.

43. The method of embodiment 42, wherein the mammalian cell is a pluripotent stem cell.

44. The method of embodiment 42, wherein the mammalian cell is a cardiomyocyte.

45. A method of synchronizing a behavior of a population of cells by introducing an electric field into a well of a plurality of wells of a microwell plate, the method comprising:
adding the population of cells in a well of the plurality of wells;
disposing a pair of electrodes within the well of the plurality of wells;
independently and axially displacing each electrode of the pair of electrodes relative to each other to enable a distal end of each electrode of the pair of electrodes to contact a bottom portion of the well;

maintaining constant contact of the distal end of each electrode of the pair of electrodes with the bottom portion of the well; and applying a uniform electric field within the well, such that the behavior of each cell of the population of cells is approximately synchronized.

46. The method of embodiment 45, wherein the population of cells comprises pluripotent cells.

47. The method of embodiment 46, wherein the behavior of the pluripotent cells after applying the uniform electric field is to further differentiate.

48. The method of embodiment 47, wherein the pluripotent cells differentiate into cardiomyocytes.

49. The method of embodiment 47, wherein the differentiated pluripotent cells exhibit at least one mature characteristic.

50. The method of embodiment 48, wherein the cardiomyocytes exhibit at least one terminally differentiated cardiomyocyte phenotype.

51. The method of any one of embodiments 45-50, wherein the population of electrically-responsive cells comprises cardiomyocytes.

52. The method of embodiment 51, wherein the behavior of the cardiomyocytes after applying the uniform electric field is beating.

53. The method of any one of embodiments 45-52, further comprising culturing the population of electrically-responsive cells.

54. An adaptive electrode arrangement for a microwell plate, the adaptive electrode arrangement comprising:
a circuit board having an opening for enabling solution to be introduced into the well and a through-hole disposed on either side of the opening; and
a pair of electrodes coupled to the circuit board and adapted to be disposed within a well of a plurality of wells, the pair of electrodes independently and axially displaceable relative to a bottom portion of the well and each other, each electrode of the pair of electrodes having a distal end and a proximal end, the proximal end disposed within the through-hole of the circuit board; and
a spring attached to the proximal end to secure the proximal end to the circuit board;
wherein the distal end of each electrode of the pair of electrodes is adapted to be in constant contact with the bottom portion of the well when disposed within the well, ensuring a uniform and constant electric field is applied within the well.

55. An adaptive electrode arrangement for a microwell plate, the adaptive electrode arrangement comprising:
a cover plate including a pair of through-holes; and
a pair of electrodes coupled to the cover plate and adapted to be disposed within a well of a plurality of wells, the pair of electrodes independently and axially displaceable relative to a an axis of the cover plate and each other, each electrode of the pair of electrodes having a distal end and a proximal end, the proximal end disposed within a through-hole of the pair of through-holes, allowing each electrode to move relative to a bottom portion of the well of the plurality of wells;
wherein the distal end of each electrode of the pair of electrodes is adapted to be in constant contact with the bottom portion of the well when disposed within the well, ensuring a uniform and constant electric field is applied within the well.

56. An adaptive electrode arrangement for a microwell plate, the adaptive electrode arrangement comprising:
a cover plate including a distal portion;
a spring having a first end and a second end, the first end attached to the distal portion of the cover plate; and
a pair of electrodes coupled to the cover plate and adapted to be disposed within a well of a plurality of wells, the pair of electrodes independently and axially displaceable relative to an axis of the cover plate and each other, each electrode of the pair of electrodes having a distal end and a proximal end, the proximal end attached to the second end of the spring, allowing each electrode to move relative to a bottom portion of the well of the plurality of wells;
wherein the distal end of each electrode of the pair of electrodes is adapted to be in constant contact with the bottom portion of the well when disposed within the well, ensuring a uniform and constant electric field is applied within the well.

57. The adaptive electrode arrangement of any of embodiments 55-56, wherein each cover plate includes an opening disposed between the pair of electrodes to allow for dispensing of solution within the well while the electric field is being applied within the well.

58. The adaptive electrode arrangement of any one of embodiments 54-56, wherein the distal end of each electrode of the pair of electrodes is adapted to be in constant contact with one or more of a bottom portion, a bottom surface, a base, or a ramp of the well.

59. The assembly of any one of embodiments 11-23, further comprising a container in which the microwell plate assembly is disposed, the container adapted to be disposed in a cell incubator system.

60. The assembly of embodiment 59, wherein the microwell plate assembly may be disconnected from electrical equipment when disposed in the cell incubator system.

61. The assembly of any one of embodiments 11-23 and 59-60, wherein each electrode of the pair of electrodes is fixed relative to one or more of each other and one of the circuit board or the cover plate.

62. The well of any one of embodiments 1-10, wherein each electrode of the pair of electrodes is fixed relative to one or more each other or one of the circuit board or the cover plate.

63. The adaptive electrode arrangement of any one of embodiments 24-30, wherein each electrode of the pair of electrodes is fixed relative to one or more of each other and one of the circuit board.

64. A method of altering a membrane potential of a cell by introducing an electric field into a well of a microwell plate assembly, the method comprising:
adding a cell in a well of the microwell plate assembly;
disposing a pair of electrodes within the well;
independently and axially displacing each electrode of the pair of electrodes relative to each other to enable a distal end of each electrode of the pair of electrodes to contact a bottom portion of the well;
maintaining constant contact of the distal end of each electrode of the pair of electrodes with the bottom portion of the well; and
applying a uniform electric field within the well, such that the membrane potential of the cell is excited.

65. The method of embodiment 64, wherein the cell comprises a pluripotent cell, and the behavior of the pluripotent cell after applying the uniform electric field is to further differentiate.

66. The method of embodiment 65, wherein the pluripotent cell differentiates into a cardiomyocyte, and the differentiated pluripotent cell exhibits at least one terminally differentiated cell phenotype.

67. The method of embodiment 66, wherein the cardiomyocyte exhibits at least one terminally differentiated cardiomyocyte phenotype.

68. The method of embodiment 67, wherein the cell comprises cardiomyocytes, and the behavior of the cardiomyocyte after applying the uniform electric field is beating.

69. The method of any one of embodiments 64-68, further comprising culturing the cell.

70. A cell incubator system comprising:
a container;
a microwell plate assembly disposed within the container, the microwell plate assembly including:
   a microwell plate having a plurality of wells; and
   an array of electrode arrangements for introducing an electric field into each well of the plurality of wells, each electrode arrangement having a pair of electrodes and one of a cover plate or a circuit board to which the pair of electrodes is coupled, each of the cover plate and the circuit board having an opening for enabling solution to be dispensed into the well while the electric field is being applied within the well.

71. The system of embodiment 70, wherein the circuit board includes a through-hole disposed on each side of the opening, the through-hole for receiving a proximal end of each electrode of the pair of electrodes.

72. The system of embodiment 70, wherein the cover plate includes a pair of through-holes, each through-hole for receiving a proximal end of each electrode of the pair of electrodes.

73. The system of any one of embodiments 70-72, the well further comprising one or more of at least one micropost, a microwire formed around the at least one micropost, a bottom surface, a base disposed on the bottom surface, and a ramp, one of extending or separate from the base, to which the at least one micropost is attached, the bottom portion including one or more of the bottom surface, the base, and the ramp.

74. The system of any one of embodiments 70-73, the well further comprising at least one micropost having a length, and each electrode of the pair of electrodes includes a length that is at least about the same or greater than the length of the at least one micropost.

75. The system of any one of embodiments 70-74, wherein the electrode arrangement includes the circuit board to which the pair of electrodes are coupled, wherein the circuit board has a configuration selected from the group consisting of:
(a) at least one section, each section including multiple arrays of electrode arrangements, each array of electrode arrangements including multiple electrode arrangements; or
(b) a single unibody, the unibody including multiple arrays of electrode arrangements, each array of electrode arrangements including multiple electrode arrangements.

76. The system of any one of embodiments 70-75, wherein each electrode of the pair of electrodes is fixed relative to one or more of each other and one of the circuit board or the cover plate.

77. A microwell plate assembly adapted to be one or more of disposed in a container of a cell incubator system or coupled to cell culture support utilities, the microwell plate assembly comprising:
a microwell plate having a plurality of wells; and
an array of electrode arrangements for introducing an electric field into each well of the plurality of wells, each electrode arrangement having a pair of electrodes and one of a cover plate or a circuit board to which the pair of electrodes is coupled, each of the cover plate and the circuit board having an opening for enabling solution to be dispensed into the well while the electric field is being applied within the well.

78. The assembly of embodiment 77, wherein the microwell plate assembly may be disconnected from electrical equipment.

79. The assembly of any one of embodiments 77-78, wherein the assembly is coupled to cell culture support utilities including one or more of a carbon dioxide element, an oxygen element, a humidified gas element, and a temperature control element.

80. The assembly of any one of embodiments 77-79, wherein the circuit board includes a through-hole disposed on each side of the opening, the through-hole for receiving a proximal end of each electrode of the pair of electrodes.

81. The assembly of any one of embodiments 77-79, wherein the cover plate includes a pair of through-holes, each through-hole for receiving a proximal end of each electrode of the pair of electrodes.

82. The assembly of any one of embodiments 77-81, the well further comprising one or more of at least one micropost, a microwire formed around the at least one micropost, a bottom surface, a base disposed on the bottom surface, and a ramp, one of extending or separate from the base, to which the at least one micropost is attached, the bottom portion including one or more of the bottom surface, the base, and the ramp.

83. The assembly of any one of embodiments 77-82, the well further comprising at least one micropost having a length, and each electrode of the pair of electrodes includes a length that is at least about the same or greater than the length of the at least one micropost.

84. The assembly of any one of embodiments 77-83, wherein each electrode of the pair of electrodes is fixed relative to one or more of each other and one of the circuit board or the cover plate.

EXAMPLES

Example 1: Cardiac Microwires Multiwell Pacing Protocol

This example demonstrates the use of an embodiment of the disclosed devices for pacing cardiac microwires ("wires") multiwall pacing of cardiomyocytes.
1. Decontaminate electrodes and circuit board
   1.1. Soak electrodes in isopropyl alcohol (IPA) prior to use for 30 minutes in biological safety cabinet (BSC).
   1.2. Spray bottom side of circuit board with IPA as well to decontaminate
   1.3. Allow electrodes to dry in BSC for at least 5' minutes.
2. Stimulator and amplifier configuration
   2.1. Configure MyoPacer Field Stimulator (IonOptix; Westwood, Mass.) with the following settings:
      2.1.1. Waveform: bipolar with 1 ms duration
      2.1.2. Voltage: 6 V
      2.1.3. Frequency: 1 Hz
   2.2. Output MyoPacer signal to stimulator by connecting Gate Out (MyoPacer) to Pulse Trigger (amplifier).
   2.3. Confirm biphasic output (waveform) and voltage amplitude of amplifier using an oscilloscope; connect amplifier output, V Monitor, to oscilloscope input.
   2.4. Send amplified amplifier output to pacing apparatus via "output pulse".

3. Electrode connection
3.1. Ensure that electrodes and circuit board are decontaminated.
3.2. Place cardiac microwire multiwell plate on base plate.
3.3. Position four standoff pins around appropriate column to be paced. These pins will be used as guide pins.
3.4. Carefully position electrodes within target wells, placing right electrodes into well first, and slowly lowering apparatus until both electrodes are within each well. Ensure alignment of circuit board holes over guide pins.
3.5. Confirm that all springs are level. If one is extended more than others, lightly tap the spring to help the electrode fall into place.
3.6. Slightly tighten the electrode with provided nuts caddy-corner from each other. Avoid overtightening nuts; tighten just enough to ensure that the electrodes will not move.
3.7. Pay close attention to springs—if the nuts are overtightened, the springs will start to push up.
3.8. Place the lid on the apparatus and feed the red and black wires out of the hole on the side of the lid.
3.9. Attach to amplifier with provided wires with the female connection.
4. Configuring MyoPacer settings
4.1. Set MyoPacer output voltage to 6 V.
4.2. Confirm that waveform is biphasic.
4.3. Set initial output frequency to 1 Hz.
5. Configuring Aurora amplifier (Aurora Scientific; Aurora, Canada) settings
5.1. Set output range to 20 V.
5.2. Set pulse phase to bi-phase.
5.3. Adjust output to 30% to achieve 6 V output (20 V*0.3) across electrode pairs in parallel circuit.
5.4 Flip an output pin to start the AC voltage signal output.
5.5 Observe the flicking of the red LED light both on Myopacer and Aurora to confirm correct output frequency.
5.6 Pacing can also be confirmed by observing the CMW pacing through the tabletop microscope (4×).

Example 2: Maturation of iPSC-Derived Cardiomyocytes within Cardiac Microwires

The goal of this experiment was to test various methods to stimulate maturation of iPSC-derived cardiomyocytes within cardiac microwires (CMWs) (also referred to as "wires"). Maturation methods included (i) culturing of CMWs in media supplemented with a low dose of isoproterenol to provide prolonged adrenergic stimulation, (ii) culturing of CMWs in media supplemented with insulin, (iii) both (i) and (ii), and (iv) accelerated pacing of CMWs via electrical field stimulation. Maturity was assessed by (a) measuring the force-frequency response (FFR), wherein CMWs were electrically stimulated at increasing frequencies. A positive FFR is desirable, as this is what is observed in mature ventricular myocardium.

CMWs were prepared and paced as described in Example 1. The different electrical stimulation conditions and results are shown in Table 2. 1. Culture media was changed every other day unless noted. Viability was assayed using calcein acetoxymethyl (AM) ester according to standard procedures.

TABLE 2.1

CMW cardiomyocyte pacing observations

| Voltage | Observations |
| --- | --- |
| 6 V | Cells dead after 1 day |
| 4 V | Cells dead after 3 days; media was yellow |
| 2 V | Cells dead after 6 days. Successfully paced up to 2 Hz, but death likely due to infrequent media changes |
| 2 V | (With culture media changes every other day) Cells observed to be alive after 4 days. Successfully paced up to 3 Hz; ceased pacing. |

Observations: for the cells paced at 6 V (1 Hz; media changed the same day as pacing), they were observed to be dead after about 20 hours of pacing. A control, which only had a single electrode (not a pair, and thus was not functional), contained a live wire, suggesting that voltage may be too high. Spiking insulin into the cultures at 20 µg/ml did not prompt the wires to resume beating.

For the cells paced at 4 V (1 Hz; media changed the day prior to pacing), they were observed to be dead after about 72 hours of pacing; however, the wires could have died earlier, but were first checked at about 72 hours. The media was yellow, suggesting an acidic environment; the control (single electrode) cells were observed to be alive. Spiking insulin into the cultures at 20 µg/ml did not prompt the wires to resume beating.

For cells paced at 2 V (1 Hz; culture media changed the day before), and then increased frequency to 2 Hz two days later, with a culture media change on the intervening day, the wires captured immediately, but stopped beating after 4 days. It was hypothesized that pacing at supernormal frequencies may require more frequent culture media changes.

For cells paced at 2 V (2 Hz with a media change the same day, then 3 Hz on the second day, with a media change the same day), the wires were observed to be beating. At this point, the wires were no longer paced.

Example 3: Automated Cardiac Microwire Media Change Protocol Using a Bravo Liquid Handler This example demonstrates the use of an embodiment of the disclosed devices for changing media of a cardiac microwire (CMW) (also referred to as "wire") plate with electrodes attached.
1. Sterilize robotic equipment
   1.1 Wipe down robotic equipment with ethanol sprayed kim wipes.
   1.2 Do not directly spray onto any robotic equipment.
2. Configure Stimulator
   2.1 Switch both current knobs on MyoPacer Field Stimulator to "off" position.
   2.2 Detach electrode cables.
3. Retrieve electrode-fitted CMW plate from incubator
4. Sterilize CMW plate and cables with ethanol sprayed kim wipes (again, not spraying directly on equipment)
5. Place electrode-fitted CMW plate on a stage area of a Bravo liquid handler (Agilent Technologies; Santa Clara, Calif.), such as stage area 6, adjacent to a center stage area of the Bravo liquid handler and remove the cover
   5.1 Make sure a bottom portion, such as a skirt, of the electrode-fitted CMW plate is aligned.
   5.2 Move CMW plate to feel out stage area boundaries for proper alignment.

6. Setup remaining labware
   6.1 Place rack of tips on a center stage area of the Bravo liquid handler, such as stage area 5, immediately adjacent to a single well reservoir also disposed in the center stage area of the Bravo liquid handler, such as in stage area 8, the single well reservoir including the fresh media.
   6.2 Remove lid from the rack of tips.
   6.3 Place one Thermo deep well reservoir (ThermoFisher Scientific; Waltham, Mass.; part no. 1064156) with 50 mL ethanol on a stage area of the Bravo liquid handler, such as stage area 1, disposed on one side of the rack of tips and another Thermo deep well reservoir w/50 mL ethanol on a stage area on the other side of the rack of tips, such as stage area 3.
7. Initialize devices
   7.1 Check that all labware is in correct location and aligned.
   7.2 Run protocol to initialize devices.
   7.3 Indicate to robot safe to proceed. 7.4 Check all tips align with electrode holes and check all angles.
   7.5 Move corner black and red electrode attachments outwards to avoid tips crashing into them.
8. Complete media change
   8.1 Aspirate media.
   8.2 Dispense into waste.
   8.3 Transfer fresh media back into CMW plate.
   8.4 Wash tips with ethanol.
9. Place cover back on CMW plate once protocol finished
10. Bring cover and CMW plate back to the incubator
11. Connect electrode cables and switch knobs back to "on" position As a control experiment to discriminate if platinum electrodes (without current) were a potential cause of cell death, electrode pairs were applied to cultures overnight without current (pacing). After overnight incubation, all such treated cultures appeared alive.

Further, while particular implementations, applications, and examples have been illustrated and described, it is to be understood that the disclosed implementations, applications, and examples are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended embodiments.

It should be understood that the legal scope of the invention is defined by the words of the embodiments set forth at the end of this patent. The appended embodiments should be construed broadly to include other variants and embodiments of same, which may be made by those skilled in the art without departing from the scope and range of equivalents of the devices, systems, methods, and their elements.

The invention claimed is:

1. A well for electrically stimulating at least one cell, the well having a bottom portion and comprising:
   an adaptive electrode arrangement for introducing an electric field into the well, the adaptive electrode arrangement including:
   a pair of electrodes disposed within the well and configured to be coupled to one of a circuit board or a cover plate, the pair of electrodes having a distal end and independently and axially displaceable relative to each other and the bottom portion of the well;
   wherein the distal end of each electrode of the pair of electrodes is in constant contact with the bottom portion of the well, ensuring one or more of a uniform or extended electric field is applied within the well, and the distal end is moveable relative to one of the circuit board or the cover plate.

2. The well of claim 1, further comprising one or more of at least one micropost, a microwire formed around the at least one micropost, a bottom surface, a base disposed on the bottom surface, and a ramp, one of extending or separate from the base, to which the at least one micropost is attached, the bottom portion including one or more of the bottom surface, the base, and the ramp, such that the distal end of each electrode of the pair of electrodes is in contact with one of the bottom surface, the base, or the ramp of the well.

3. The well of claim 1, the well further comprising at least one micropost having a length, and each electrode of the pair of electrodes includes a length that is at least about the same or greater than the length of the at least one micropost.

4. The well of claim 1, wherein the adaptive electrode arrangement is adapted to be integrated to the circuit board, the circuit board including a plurality of openings and a through-hole disposed on either side of each opening, the through-hole for receiving a proximal end of each electrode of the pair of electrodes, and wherein each electrode of the pair of electrodes is fixed relative to the circuit board.

5. The well of claim 1, further comprising a spring for securing each proximal end of each electrode of the pair of electrodes to the circuit board and enabling each electrode to be independently and axially displaceable, wherein each electrode of the pair of electrodes is disposed on either side of an opening of the plurality of openings of the circuit board.

6. The well of claim 1, wherein the adaptive electrode arrangement further includes the cover plate, and the cover plate includes a pair of through-holes, each through-hole for receiving a proximal end of each electrode of the pair of electrodes, and each electrode axially displaceable along an axis of the cover plate, allowing each electrode to move relative to one or more of the bottom portion of the well and the cover plate, and wherein each cover plate includes an opening disposed between the pair of electrodes to allow for dispensing of solution within the well while the electric field is being applied within the well.

7. The well of claim 1, wherein the adaptive electrode arrangement further includes the cover plate, and the cover plate includes a distal portion, each electrode of the pair of electrodes having a proximal end, and the adaptive electrode arrangement further comprising a spring with a first end attached to the distal portion of the cover plate and a second end coupled to the proximal end of each electrode of the pair of electrodes to couple each electrode to the cover plate, allowing each electrode to be axially displaceable along an axis of the cover plate.

8. The well of claim 6, wherein the distal end of each electrode of the pair of electrodes is in constant contact with the bottom portion of the well, the bottom portion of the well including one or more of a bottom surface, a base, or a ramp of the well, or wherein the bottom portion of the well is one or more of flat, convex or concave.

* * * * *